US012788958B2

(12) United States Patent
Brand et al.

(10) Patent No.: US 12,788,958 B2
(45) Date of Patent: Nov. 10, 2026

(54) SYSTEM, METHOD, AND PRODUCT FOR EVENT MONITORING

(71) Applicant: Becton, Dickinson and Company, Franklin Lakes, NJ (US)

(72) Inventors: Maarten Brand, Ridgewood, NJ (US); Mark Andrew Nelson, Harrison, NJ (US); Jack Balji, Mahwah, NJ (US); Philip Ponce de Leon, Brooklyn, NY (US); Erik Kurt Witt, Oakland, NJ (US); Ray Isaacson, Layton, UT (US); Ashley Rachel Rothenberg, Morris Plains, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1335 days.

(21) Appl. No.: 17/421,997

(22) PCT Filed: Feb. 4, 2020

(86) PCT No.: PCT/US2020/016539
§ 371 (c)(1),
(2) Date: Jul. 9, 2021

(87) PCT Pub. No.: WO2020/163297
PCT Pub. Date: Aug. 13, 2020

(65) Prior Publication Data

US 2022/0118240 A1 Apr. 21, 2022

Related U.S. Application Data

(60) Provisional application No. 62/800,613, filed on Feb. 4, 2019.

(51) Int. Cl.
*A61M 39/06* (2006.01)
*A61M 39/10* (2006.01)
(Continued)

(52) U.S. Cl.
CPC ........ *A61M 39/16* (2013.01); *A61M 39/0613* (2013.01); *A61M 39/26* (2013.01);
(Continued)

(58) Field of Classification Search
CPC . G16H 20/17; A61M 5/16854; A61M 5/3146; A61M 39/06; A61M 39/10;
(Continued)

(56) References Cited

U.S. PATENT DOCUMENTS

| | | | |
|---|---|---|---|
| 4,730,536 | A | 3/1988 | Nordmann |
| 5,218,965 | A | 6/1993 | Ring |

(Continued)

FOREIGN PATENT DOCUMENTS

| | | | |
|---|---|---|---|
| CN | 203263863 | U | 11/2013 |
| CN | 106029158 | A | 10/2016 |

(Continued)

*Primary Examiner* — Michael J Tsai
*Assistant Examiner* — Forrest B Dipert
(74) *Attorney, Agent, or Firm* — The Webb Law Firm

(57) ABSTRACT

A signal measured by a sensor connected to a needleless connector including a fluid flow path may be obtained to determine, based on the signal, an event associated with the needleless connector, such as at least one of: a scrubbing event in which the needleless connector is scrubbed with a disinfectant, a flushing event in which the needleless connector is flushed with a solution, a connection event in which the needleless connector is connected to a medical device, a disconnection event in which the needleless connector is disconnected from the medical device, or any combination thereof. An indication of the determined event may be provided.

28 Claims, 15 Drawing Sheets

(51) Int. Cl.
*A61M 39/16* (2006.01)
*A61M 39/26* (2006.01)

(52) U.S. Cl.
CPC ................. *A61M 2039/062* (2013.01); *A61M 2039/1005* (2013.01); *A61M 2039/1044* (2013.01); *A61M 2205/3306* (2013.01); *A61M 2205/332* (2013.01); *A61M 2205/3334* (2013.01)

(58) Field of Classification Search
CPC ............ A61M 39/16; A61M 2039/066; A61M 2039/1005; A61M 2039/1044; A61M 2039/1072; A61M 2205/332; A61M 2205/3331; A61M 2205/50; A61M 2205/583; A61M 2205/6054; A61M 2205/6063
See application file for complete search history.

(56) References Cited

U.S. PATENT DOCUMENTS

| | | | | |
|---|---|---|---|---|
| 5,881,717 | A * | 3/1999 | Isaza | A61M 16/0051 128/204.21 |
| 8,221,391 | B2 | 7/2012 | Fangrow, Jr. | |
| 9,816,966 | B2 | 11/2017 | Sagebiel | |
| 10,143,830 | B2 * | 12/2018 | Bochenko | A61M 39/162 |
| 2005/0197585 | A1 * | 9/2005 | Brockway | A61B 5/411 600/561 |
| 2010/0198141 | A1 | 8/2010 | Laitenberger et al. | |
| 2011/0315757 | A1 | 12/2011 | Colman et al. | |
| 2012/0240686 | A1 * | 9/2012 | Blomberg | G01L 19/003 73/756 |
| 2013/0297222 | A1 * | 11/2013 | Callicoat | G16B 99/00 702/19 |
| 2013/0323117 | A1 | 12/2013 | Ma et al. | |
| 2014/0221911 | A1 * | 8/2014 | Van Wieren | A61M 1/3659 604/65 |
| 2015/0165185 | A1 | 6/2015 | Cohen et al. | |
| 2018/0028755 | A1 | 2/2018 | Philip et al. | |
| 2018/0193629 | A1 | 7/2018 | Grant et al. | |

FOREIGN PATENT DOCUMENTS

| | | | | |
|---|---|---|---|---|
| CN | 108024729 | B | 9/2021 | |
| JP | H0623058 | A | 2/1994 | |
| JP | 2005515849 | A | 6/2005 | |
| JP | 2009247404 | A | 10/2009 | |
| JP | 2016512114 | A | 4/2016 | |
| JP | 2016515451 | A | 5/2016 | |
| JP | 2017502774 | A | 1/2017 | |
| JP | 2018134475 | A | 8/2018 | |
| JP | 2019501741 | A | 1/2019 | |
| WO | 2014159928 | A1 | 10/2014 | |
| WO | 2014173770 | A1 | 10/2014 | |
| WO | WO-2017053882 | A1 * | 3/2017 | A61B 5/0022 |
| WO | 2018022640 | A1 | 2/2018 | |
| WO | 2018144369 | A1 | 8/2018 | |
| WO | 2019204153 | A1 | 10/2019 | |

* cited by examiner

SYSTEM, METHOD, AND PRODUCT FOR EVENT MONITORING

CROSS-REFERENCE TO RELATED APPLICATIONS

This application is the United States national phase of International Application No. PCT/US2020/016539 filed Feb. 4, 2020, and claims priority to U.S. Provisional Application No. 62/800,613, entitled "System, Method, and Product for Event Monitoring", filed Feb. 4, 2019. The entire disclosures of which are hereby incorporated by reference.

BACKGROUND

Drug Infusion into a human body is often achieved through catheters that are either inserted into a peripheral vein (PIVC) or central vein (PICC/CVC). A catheter may be connected to a pump via a needleless connector.

Proper catheter maintenance may include scrubbing a needleless connector with a disinfectant upon every disconnection/connection, regular flushing of the line with flush solution to minimize build-up of residue, and/or use of disinfectant caps when a needleless connector is not in use. These maintenance activities may be performed routinely as part of catheter maintenance, in conjunction with IV line connections and disconnections, medication pushes from syringes, blood draws, and/or the like. Proper catheter maintenance helps to (i) reduce or prevent harmful bacteria from accumulating and being infused into the human body (e.g., the infusion of harmful bacteria may result in Catheter Related Blood Stream Infection (CRBSI), etc.) and/or Central Line-associated Bloodstream Infection (CLABSI), which are associated with high mortality rate and can cause a significant cost burden to a hospital due to extended patient lengths of stay; and (ii) minimize a chance of occlusion of the catheter (e.g., occlusion has shown to lead to increased risk of CRBSI by providing an inoculation ground for harmful bacteria and may require use of drugs to dissolve occlusion or lead to replacement of the catheter, which further increases patient safety risk due to increased CRBSI and additional costs to the hospital, etc.)

Hospitals and homecare patient environments (e.g., in which nurses, caregivers, patient maintenance activities, etc. can be monitored) have adopted protocols that are aimed at ensuring proper catheter maintenance. However, multiple studies have shown poor adherence to these existing protocols, leading to sub-optimal patient outcomes.

SUMMARY

Accordingly, provided are improved systems, devices, products, apparatus, and/or methods for event monitoring.

According to some non-limiting embodiments or aspects, provided is a system including a needleless connector including a fluid flow path; one or more force sensors connected to the needleless connector; and one or more processors programmed and/or configured to: receive, from the force sensor, a force signal; and determine, based on the force signal, at least one of: a scrubbing event in which the needleless connector is scrubbed with a disinfectant, a flushing event in which the needleless connector is flushed with a solution, a connection event in which the needleless connector is connected to a medical device, a disconnection event in which the needleless connector is disconnected from the medical device, or any combination thereof.

In some non-limiting embodiments or aspects, the system further includes communication circuitry configured to transmit the force signal to a remote computing system.

In some non-limiting embodiments or aspects, the force sensor includes at least one of: a piezoelectric element, a force sensitive resistive (FSR) sensor, a strain gauge, or any combination thereof.

In some non-limiting embodiments or aspects, the force sensor is positioned between an outer surface of an inner wall of the needleless connector defining the fluid flow path of the needleless connector and an inner surface of an outer wall of the needleless connector surrounding the inner wall of the needleless connector.

In some non-limiting embodiments or aspects, the force sensor includes a plurality of force sensors positioned around the fluid flow path of the needleless connector between the inner wall of the needleless connector defining the fluid flow path of the needleless connector and the inner surface of the outer wall of the needleless connector surrounding the inner wall of the needleless connector.

In some non-limiting embodiments or aspects, a first end of the needleless connector includes a septum including a surface facing in a first direction, wherein the force sensor is configured to detect a force in a second direction perpendicular to the surface of the septum facing in the first direction, and wherein the one or more processors are further programmed and/or configured to: determine, based on the force signal indicating periodic forces in the second direction perpendicular to the surface of the septum facing in the first direction, the flushing event, wherein the flushing event includes a pulsatile flushing event.

In some non-limiting embodiments or aspects, the force sensor includes a pressure sensor, wherein the pressure sensor is one of: in direct contact with a fluid in the fluid flow path of the needleless connector; located within an inner wall of the needleless connector defining the fluid flow path of the needleless connector, and located within a wall of a lumen connected to the needleless connector.

In some non-limiting embodiments or aspects, the system further includes: an optical sensor configured to detect at least one of a color signature and a reflectance of the medical device, and wherein the one or more processors are further programmed and/or configured to: determine, based on the at least one of the color signature and the reflectance of the medical device, a type of the medical device.

In some non-limiting embodiments or aspects, an optical sensor may detect machine-readable information (e.g., a bar code) which can be used to identify a device, a device family, or a unique individual device, and/or the like.

In some non-limiting embodiments or aspects, the one or more processors are further programmed or configured to: determine, based on the force signal, a pattern of events including a plurality of the least one of: the scrubbing event in which the needleless connector is scrubbed with the disinfectant, the flushing event in which the needleless connector is flushed with the solution, the connection event in which the needleless connector is connected to the medical device, the disconnection event in which the needleless connector is disconnected from the medical device, or any combination thereof; and determine, based on the pattern of events, a medication administration event in which a medication is administered to a patient via the needleless connector.

In some non-limiting embodiments or aspects, the system further includes: an identification sensor configured to detect an identification tag on a medical device connected to or being connected to the needleless connector.

In some non-limiting embodiments or aspects, the identification sensor includes a magnetometer, and wherein the identification tag includes a magnetic material.

In some non-limiting embodiments or aspects, the system further includes a positional sensor configured to detect movement of the needleless connector, wherein the one or more processors are further programmed and/or configured to: determine, based on the detected movement of the needleless connector, at least one of: a movement of the patient and a movement of a bed of the patient.

In some non-limiting embodiments or aspects, the system further includes: a color sensor configured to detect a color of a fluid in the fluid flow path of the needleless connector, wherein the one or more processors are further programmed and/or configured to: determine, based on the color of the fluid detected in the fluid flow path of the needleless connector, at least one of a blood-draw in the needleless connector and a retention of blood in the needleless connector.

In some non-limiting embodiments or aspects, the system further includes: a visual indicator configured to provide a visual indication associated with the at least one of: the scrubbing event in which the needleless connector is scrubbed with the disinfectant, the flushing event in which the needleless connector is flushed with the solution, the connection event in which the needleless connector is connected to the medical device, the disconnection event in which the needleless connector is disconnected from the medical device, or any combination thereof.

According to some non-limiting embodiments or aspects, provided is a method including: measuring, with a force sensor connected to a needleless connector including a fluid flow path, a force signal; receiving, with at least one processor from the force sensor, the force signal; and determining, with at least one processor, based on the force signal, at least one of: a scrubbing event in which the needleless connector is scrubbed with a disinfectant, a flushing event in which the needleless connector is flushed with a solution, a connection event in which the needleless connector is connected to a medical device, a disconnection event in which the needleless connector is disconnected from the medical device, or any combination thereof.

In some non-limiting embodiments or aspects, the method further includes: transmitting, with communication circuitry, the force signal to a remote computing system.

In some non-limiting embodiments or aspects, the force sensor includes at least one of: a piezoelectric element, a force sensitive resistive (FSR) sensor, a strain gauge, or any combination thereof.

In some non-limiting embodiments or aspects, the force sensor is positioned between an outer surface of an inner wall of the needleless connector defining the fluid flow path of the needleless connector and an inner surface of an outer wall of the needleless connector surrounding the inner wall of the needleless connector.

In some non-limiting embodiments or aspects, the force sensor includes a plurality of force sensors positioned around the fluid flow path of the needleless connector between the inner wall of the needleless connector defining the fluid flow path of the needleless connector and the inner surface of the outer wall of the needleless connector surrounding the inner wall of the needleless connector.

In some non-limiting embodiments or aspects, a first end of the needleless connector includes a septum including a surface facing in a first direction, wherein the force sensor is configured to detect a force in a second direction perpendicular to the surface of the septum facing in the first direction, and wherein the method further includes: determining, with at least one processor, based on the force signal indicating periodic forces in the second direction perpendicular to the surface of the septum facing in the first direction, the flushing event, wherein the flushing event includes a pulsatile flushing event.

In some non-limiting embodiments or aspects, the force sensor includes a pressure sensor, wherein the pressure sensor is one of: in direct contact with a fluid in the fluid flow path of the needleless connector; located within an inner wall of the needleless connector defining the fluid flow path of the needleless connector, and located within a wall of a lumen connected to the needleless connector.

In some non-limiting embodiments or aspects, the method further includes: detecting, with an optical sensor, at least one of a color signature and a reflectance of the medical device; and determining, with at least one processor, based on the at least one of the color signature and the reflectance of the medical device, a type of the medical device.

In some non-limiting embodiments or aspects, the method further includes: determining, with at least one processor, based on the force signal, a pattern of events including a plurality of the least one of: the scrubbing event in which the needleless connector is scrubbed with the disinfectant, the flushing event in which the needleless connector is flushed with the solution, the connection event in which the needleless connector is connected to the medical device, the disconnection event in which the needleless connector is disconnected from the medical device, or any combination thereof; and determining, with at least one processor, based on the pattern of events, a medication administration event in which a medication is administered to a patient via the needleless connector.

In some non-limiting embodiments or aspects, a force sensor for determining an event or a pattern of events based on the force signal includes a force sensor, a pressure sensor, a strain gauge or sensor, an accelerometer, an acoustic sensor, a microphone, a force sensitive resistor (FSR), a stress sensor, or any combination thereof to measure a signal or signals. A signal or signals measured may be a result of interaction of a user with a device (e.g., a smart device, a needleless connector, a lumen, etc.) when the user handles the device, which can cause forces which can be measured by the force sensor, the pressure sensor, the strain sensor, the stress sensors, or any combination thereof. In some non-limiting embodiments or aspects, forces may be created which are at a relatively higher frequency in nature, such as forces that may be referred to vibrations and/or acoustics. For example, scrubbing a connector may create relatively lower frequency signals (e.g., signal less than 20 Hz, etc.) from user handling, and relatively higher frequency forces from a rubbing interaction of a swab with the surface of the connector.

Alternatively to, or in addition to, direct measurements of forces with a transducer and/or the like, measurements of changes in connector components can be used to indicate how a device (e.g., a needleless connector, a smart device, a lumen, etc.) is used or being used. For example, in a needleless connector the central valve, or membrane may be compressed along a central axis when a connection to another medical device is formed, and the compression of the membrane may be measured using optical and/or other encoding techniques (e.g., to determine an amount of compression, a distance of compression, a frequency of compression, a time of compression, a frequency, etc.).

In some non-limiting embodiments or aspects, a chemical sensor, a wetness sensor, an impedance sensor, a temperature sensor, or any combination thereof may be used to determine and/or indicate a fluid on a surface of a needleless connector and/or a smart device. For example, a chemical sensor, a wetness sensor, an impedance sensor, a temperature sensor, or any combination thereof may be employed to differentiate alcohol as the alcohol evaporates from a lumen (e.g., an IV fluid), and/or the like.

In some non-limiting embodiments or aspects, the method further includes: detecting, with an identification sensor, an identification tag on a medical device connected to or being connected to the needleless connector.

In some non-limiting embodiments or aspects, the identification sensor includes a magnetometer, and wherein the identification tag includes a magnetic material.

In some non-limiting embodiments or aspects, the method further includes: detecting, with a position sensor, one or more gyroscopes, one or more accelerometers, or any combination thereof, movement of the needleless connector; and determining, with at least one processor, based on the detected movement of the needleless connector, at least one of: a movement of the patient and a movement of a bed of the patient.

In some non-limiting embodiments or aspects, the method further includes: detecting, with a color sensor, a color of a fluid in the fluid flow path of the needleless connector; and determining, based on the color of the fluid detected in the fluid flow path of the needleless connector, at least one of a blood-draw in the needleless connector and a retention of blood in the needleless connector.

In some non-limiting embodiments or aspects, the method further includes: providing, with a visual indicator, a visual indication associated with the at least one of: the scrubbing event in which the needleless connector is scrubbed with the disinfectant, the flushing event in which the needleless connector is flushed with the solution, the connection event in which the needleless connector is connected to the medical device, the disconnection event in which the needleless connector is disconnected from the medical device, or any combination thereof.

According to some non-limiting embodiments or aspects, provided is a needleless connector, including: a fluid flow path; a force sensor configured to measure a force signal; a visual indicator; and one or more processors programmed and/or configured to: receive, from the force sensor, a force signal; determine, based on the force signal, at least one of: a scrubbing event in which the needleless connector is scrubbed with a disinfectant, a flushing event in which the needleless connector is flushed with a solution, a connection event in which the needleless connector is connected to a medical device, a disconnection event in which the needleless connector is disconnected from the medical device, or any combination thereof; and control the visual indicator to provide a visual indication associated with the at least one of: the scrubbing event in which the needleless connector is scrubbed with the disinfectant, the flushing event in which the needleless connector is flushed with the solution, the connection event in which the needleless connector is connected to the medical device, the disconnection event in which the needleless connector is disconnected from the medical device, or any combination thereof.

In some non-limiting embodiments or aspects, the force sensor is positioned between an outer surface of an inner wall of the needleless connector defining the fluid flow path of the needleless connector and an inner surface of an outer wall of the needleless connector surrounding the inner wall of the needleless connector.

According to some non-limiting embodiments or aspects, provided is a computer program product including at least one non-transitory computer-readable medium including program instructions that, when executed by at least one processor, cause the at least one processor to: obtain a force signal measured by a force sensor connected to a needleless connector including a fluid flow path; determine, based on the force signal, at least one of: a scrubbing event in which the needleless connector is scrubbed with a disinfectant, a flushing event in which the needleless connector is flushed with a solution, a connection event in which the needleless connector is connected to a medical device, a disconnection event in which the needleless connector is disconnected from the medical device, or any combination thereof; and provide an indication of the determined event.

According to some non-limiting embodiments or aspects provided is a system, including: a needleless connector including a fluid flow path; an acoustic sensor connected to the needleless connector; and one or more processors programmed and/or configured to: receive, from the acoustic sensor, a signal including a sound signature; and determine, based on the signal, an event associated with the needleless connector.

In some non-limiting embodiments or aspects, the event associated with the needleless connector includes a connection event in which the needleless connector is connected to a medical device, and wherein the one or more processors are further programmed and/or configured to determine, based on the sound signature, a type of the medical device connected to the needleless connector from a plurality of types of medical devices.

In some non-limiting embodiments or aspects, the plurality of types of medical devices includes two or more of the following: a cap, a syringe, a tubing, a medical device connector, or any combination thereof.

In some non-limiting embodiments or aspects, the one or more processors are further programmed and/or configured to determine, based on the sound signature, a subtype of the determined type of the medical device connected to the needleless connector from a plurality of subtypes of that type of medical device.

In some non-limiting embodiments or aspects, the event associated with the needleless connector includes an operation of a medical device connected to the needleless connector, and wherein the one or more processors are further programmed and/or configured to determine, based on the sound signature, a state of the medical device connected to the needleless connector.

In some non-limiting embodiments or aspects, the state of the medical device includes an unused state or a used state.

In some non-limiting embodiments or aspects, the medical device includes a syringe, and wherein the operation of the syringe includes a depression of a plunger of the syringe into a barrel of the syringe, and wherein the depression of the plunger of the syringe into the barrel of the syringe generates the sound signature.

In some non-limiting embodiments or aspects, the plunger of the syringe includes one or more extrusions that generate the sound signature in combination with the barrel of the syringe when the plunger of the syringe is depressed into the barrel of the syringe.

In some non-limiting embodiments or aspects, the state of the medical device includes a volume of fluid expelled from the syringe when the plunger of the syringe is depressed into the barrel of the syringe.

In some non-limiting embodiments or aspects, the medical device includes a disinfectant cap.

In some non-limiting embodiments or aspects, the disinfectant cap includes a switch, and wherein the operation of the disinfectant cap includes a connection of the disinfectant cap to the needleless connector, and wherein connection of the disinfectant cap to the needleless connector generates the sound signature when the state of the disinfectant cap includes the unused state, and wherein, when the state of the disinfectant cap includes the used state, the connection of the disinfectant cap to the needleless connector one of: (i) does not generate the sound signature and (ii) generates another sound signature different than the sound signature generated when the state of the disinfectant cap includes the unused state.

In some non-limiting embodiments or aspects, the switch includes a bi-stable metal dome switch.

According to some non-limiting embodiments or aspects, provided is a system, including: a needleless connector including a fluid flow path and a septum; an optical sensor connected to the needleless connector, wherein the optical sensor is configured to detect a movement of the septum; and one or more processors programmed and/or configured to: receive, from the optical sensor, a signal associated with the movement of the septum; and determine, based on the signal, an event associated with the needleless connector.

In some non-limiting embodiments or aspects, the event associated with the needleless connector includes at least one of: a connection event in which the needleless connector is connected to a medical device, a disconnection event in which the needleless connector is disconnected from the medical device.

In some non-limiting embodiments or aspects, the septum includes one or more markings, and wherein the optical sensor is configured to detect a movement of the one or more markings to detect the movement of the septum.

In some non-limiting embodiments or aspects, the optical sensor is further configured to detect at least one of a color signature and a reflectance of the medical device, and wherein the one or more processors are further programmed and/or configured to determine, based on the at least one of the color signature and the reflectance of the medical device, a type of the medical device.

According to some non-limiting embodiments or aspects, provided is a system, including: a needleless connector including a fluid flow path, wherein the needleless connector is connected to catheter hub of a catheter including a catheter lumen and a needle tip for delivering fluid to a patient at an opposite end of the catheter lumen from the catheter hub; a pressure sensor connected to the needleless connector, wherein the pressure sensor is configured to sense a pressure transmitted through at least one of a fluid in the catheter and a material of the catheter; and one or more processors programmed and/or configured to: receive, from the pressure sensor, a signal associated with the sensed pressure; and determine, based on the signal, an event associated with the catheter.

In some non-limiting embodiments or aspects, the event associated with the catheter includes a time at which the needle tip of the catheter enters a blood vessel of the patient, and wherein the one or more processors are programmed and/or configured to determine the time at which the needle tip of the catheter enters the blood vessel based on at least one: of a heart rate, a respiration rate, a blood pressure, a penetration force of the needle tip, or any combination thereof, determined from the signal associated with the sensed pressure.

In some non-limiting embodiments or aspects, the event associated with the catheter includes a clamping sequence, and wherein the one or more processors are programmed and/or configured to determine the clamping sequence based on one or more changes over time in the signal associated with the sensed pressure.

In some non-limiting embodiments or aspects, the one or more processors are programmed and/or configured to determine, based on the determined clamping sequence and a type of the needleless connector, whether the determined clamping sequence satisfies a clamping protocol associated with the type of the needleless connector.

In some non-limiting embodiments or aspects, the event associated with the catheter includes an occlusion of the catheter lumen, and wherein the one or more processors are programmed and/or configured to determine the occlusion of the catheter lumen based on a rate of change in the sensed pressure.

Further non-limiting embodiments or aspects are set forth in the following numbered clauses:

Clause 1. A system, comprising: a needleless connector including a fluid flow path; a force sensor connected to the needleless connector; and one or more processors programmed and/or configured to: receive, from the force sensor, a force signal; and determine, based on the force signal, at least one of: a scrubbing event in which the needleless connector is scrubbed with a disinfectant, a flushing event in which the needleless connector is flushed with a solution, a connection event in which the needleless connector is connected to a medical device, a disconnection event in which the needleless connector is disconnected from the medical device, or any combination thereof.

Clause 2. The system of clause 1, further comprising: communication circuitry configured to transmit the force signal to a remote computing system.

Clause 3. The system of any of clauses 1 and 2, wherein the force sensor includes at least one of: a piezoelectric element, a force sensitive resistive (FSR) sensor, a strain gauge, or any combination thereof. In some non-limiting embodiments or aspects, the force sensor may include an accelerometer, a gyroscope, an acoustic sensor, a microphone, and/or the like. For example, a force signal measured by the force sensor may be used in combination with information and/or data measured by accelerometers and/or gyroscopes to determine movement events and classify the movement events as a repositioning of a patient, a fall of a patient, and/or the like.

Clause 4. The system of any of clauses 1-3, wherein the force sensor is positioned between an outer surface of an inner wall of the needleless connector defining the fluid flow path of the needleless connector and an inner surface of an outer wall of the needleless connector surrounding the inner wall of the needleless connector.

Clause 5. The system of any of clauses 1-4, wherein the force sensor comprises a plurality of force sensors positioned around the fluid flow path of the needleless connector between the inner wall of the needleless connector defining the fluid flow path of the needleless connector and the inner surface of the outer wall of the needleless connector surrounding the inner wall of the needleless connector.

Clause 6. The system of any of clauses 1-5, wherein a first end of the needleless connector includes a septum including a surface facing in a first direction, wherein the force sensor is configured to detect a force in a second direction perpendicular to the surface of the septum facing in the first direction, and wherein the one or more processors are further programmed and/or configured to: determine, based on the force signal indicating periodic forces in the second direction perpendicular to the surface of the septum facing in the first direction, the flushing event, wherein the flushing event includes a pulsatile flushing event.

Clause 7. The system of any of clauses 1-6, wherein the force sensor includes a pressure sensor, wherein the pressure sensor is one of: in direct contact with a fluid in the fluid flow path of the needleless connector; located within an inner wall of the needleless connector defining the fluid flow path of the needleless connector, and located within a wall of a lumen connected to the needleless connector.

Clause 8. The system of any of clauses 1-7, further comprising: an optical sensor configured to detect at least one of a color signature and a reflectance of the medical device, and wherein the one or more processors are further programmed and/or configured to: determine, based on the at least one of the color signature and the reflectance of the medical device, a type of the medical device.

Clause 9. The system of any of clauses 1-8, wherein the one or more processors are further programmed or configured to: determine, based on the force signal, a pattern of events including a plurality of the least one of: the scrubbing event in which the needleless connector is scrubbed with the disinfectant, the flushing event in which the needleless connector is flushed with the solution, the connection event in which the needleless connector is connected to the medical device, the disconnection event in which the needleless connector is disconnected from the medical device, or any combination thereof; and determine, based on the pattern of events, a medication administration event in which a medication is administered to a patient via the needleless connector.

Clause 10. The system of any of clauses 1-9, further comprising: an identification sensor configured to detect an identification tag on a medical device connected to or being connected to the needleless connector.

Clause 11. The system of any of clauses 1-10, wherein the identification sensor includes a magnetometer, and wherein the identification tag includes a magnetic material.

Clause 12. The system of any of clauses 1-11, further comprising: a positional sensor configured to detect movement of the needleless connector, wherein the one or more processors are further programmed and/or configured to: determine, based on the detected movement of the needleless connector, at least one of: a movement of the patient and a movement of a bed of the patient.

Clause 13. The system of any of clauses 1-12, further comprising: a color sensor configured to detect a color of a fluid in the fluid flow path of the needleless connector, wherein the one or more processors are further programmed and/or configured to: determine, based on the color of the fluid detected in the fluid flow path of the needleless connector, at least one of a blood-draw in the needleless connector and a retention of blood in the needleless connector.

Clause 14. The system of any of clauses 1-13, further comprising: a visual indicator configured to provide a visual indication associated with the at least one of: the scrubbing event in which the needleless connector is scrubbed with the disinfectant, the flushing event in which the needleless connector is flushed with the solution, the connection event in which the needleless connector is connected to the medical device, the disconnection event in which the needleless connector is disconnected from the medical device, or any combination thereof.

Clause 15. A method, comprising: measuring, with a force sensor connected to a needleless connector including a fluid flow path, a force signal; receiving, with at least one processor from the force sensor, the force signal; and determining, with at least one processor, based on the force signal, at least one of: a scrubbing event in which the needleless connector is scrubbed with a disinfectant, a flushing event in which the needleless connector is flushed with a solution, a connection event in which the needleless connector is connected to a medical device, a disconnection event in which the needleless connector is disconnected from the medical device, or any combination thereof.

Clause 16. The method of clause 15, further comprising: transmitting, with communication circuitry, the force signal to a remote computing system.

Clause 17. The method of any of clauses 15 and 16, wherein the force sensor includes at least one of: a piezoelectric element, a force sensitive resistive (FSR) sensor, a strain gauge, or any combination thereof.

Clause 18. The method of any of clauses 15-17, wherein the force sensor is positioned between an outer surface of an inner wall of the needleless connector defining the fluid flow path of the needleless connector and an inner surface of an outer wall of the needleless connector surrounding the inner wall of the needleless connector.

Clause 19. The method of any of clauses 15-18, wherein the force sensor comprises a plurality of force sensors positioned around the fluid flow path of the needleless connector between the inner wall of the needleless connector defining the fluid flow path of the needleless connector and the inner surface of the outer wall of the needleless connector surrounding the inner wall of the needleless connector.

Clause 20. The method of any of clauses 15-19, wherein a first end of the needleless connector includes a septum including a surface facing in a first direction, wherein the force sensor is configured to detect a force in a second direction perpendicular to the surface of the septum facing in the first direction, and wherein the method further comprises: determining, with at least one processor, based on the force signal indicating periodic forces in the second direction perpendicular to the surface of the septum facing in the first direction, the flushing event, wherein the flushing event includes a pulsatile flushing event.

Clause 21. The method of any of clauses 15-20, wherein the force sensor includes a pressure sensor, wherein the pressure sensor is one of: in direct contact with a fluid in the fluid flow path of the needleless connector; located within an inner wall of the needleless connector defining the fluid flow path of the needleless connector, and located within a wall of a lumen connected to the needleless connector.

Clause 22. The method of any of clauses 15-21, further comprising: detecting, with an optical sensor, at least one of a color signature and a reflectance of the medical device; and determining, with at least one processor, based on the at least one of the color signature and the reflectance of the medical device, a type of the medical device.

Clause 23. The method of any of clauses 15-22, further comprising: determining, with at least one processor, based on the force signal (and/or information and/or data from one or more gyroscopes and/or one or more accelerometers, etc.), a pattern of events including a plurality of the least one of: the scrubbing event in which the needleless connector is scrubbed with the disinfectant, the flushing event in which the needleless connector is flushed with the solution, the connection event in which the needleless connector is connected to the medical device, the disconnection event in which the needleless connector is disconnected from the medical device, or any combination thereof; and determining, with at least one processor, based on the pattern of events, a medication administration event in which a medication is administered to a patient via the needleless connector.

Clause 24. The method of any of clauses 15-23, further comprising: detecting, with an identification sensor, an identification tag on a medical device connected to or being connected to the needleless connector.

Clause 25. The method of any of clauses 15-24, wherein the identification sensor includes a magnetometer, and wherein the identification tag includes a magnetic material.

Clause 26. The method of any of clauses 15-25, further comprising: detecting, with a positional sensor, movement of the needleless connector; and determining, with at least one processor, based on the detected movement of the needleless connector, at least one of: a movement of the patient and a movement of a bed of the patient.

Clause 27. The method of any of clauses 15-26, further comprising: detecting, with a color sensor, a color of a fluid in the fluid flow path of the needleless connector; and determining, based on the color of the fluid detected in the fluid flow path of the needleless connector, at least one of a blood-draw in the needleless connector and a retention of blood in the needleless connector.

Clause 28. The method of any of clause 15-27, further comprising: providing, with a visual indicator, a visual indication associated with the at least one of: the scrubbing event in which the needleless connector is scrubbed with the disinfectant, the flushing event in which the needleless connector is flushed with the solution, the connection event in which the needleless connector is connected to the medical device, the disconnection event in which the needleless connector is disconnected from the medical device, or any combination thereof.

Clause 29. A needleless connector, comprising: a fluid flow path; a force sensor configured to measure a force signal; a visual indicator; and one or more processors programmed and/or configured to: receive, from the force sensor, a force signal; determine, based on the force signal, at least one of: a scrubbing event in which the needleless connector is scrubbed with a disinfectant, a flushing event in which the needleless connector is flushed with a solution, a connection event in which the needleless connector is connected to a medical device, a disconnection event in which the needleless connector is disconnected from the medical device, or any combination thereof; and control the visual indicator to provide a visual indication associated with the at least one of: the scrubbing event in which the needleless connector is scrubbed with the disinfectant, the flushing event in which the needleless connector is flushed with the solution, the connection event in which the needleless connector is connected to the medical device, the disconnection event in which the needleless connector is disconnected from the medical device, or any combination thereof.

Clause 30. The needleless connector of clause 29, wherein the force sensor is positioned between an outer surface of an inner wall of the needleless connector defining the fluid flow path of the needleless connector and an inner surface of an outer wall of the needleless connector surrounding the inner wall of the needleless connector.

Clause 31. A computer program product comprising at least one non-transitory computer-readable medium including program instructions that, when executed by at least one processor, cause the at least one processor to: obtain a force signal measured by a force sensor connected to a needleless connector including a fluid flow path; determine, based on the force signal, at least one of: a scrubbing event in which the needleless connector is scrubbed with a disinfectant, a flushing event in which the needleless connector is flushed with a solution, a connection event in which the needleless connector is connected to a medical device, a disconnection event in which the needleless connector is disconnected from the medical device, or any combination thereof; and provide an indication of the determined event.

Clause 32. A system, comprising: a needleless connector including a fluid flow path; an acoustic sensor connected to the needleless connector; and one or more processors programmed and/or configured to: receive, from the acoustic sensor, a signal including a sound signature; and determine, based on the signal, an event associated with the needleless connector.

Clause 33. The system of clause 32, wherein the event associated with the needleless connector includes a connection event in which the needleless connector is connected to a medical device, and wherein the one or more processors are further programmed and/or configured to determine, based on the sound signature, a type of the medical device connected to the needleless connector from a plurality of types of medical devices.

Clause 34. The system of any of clauses 32 and 33, wherein the plurality of types of medical devices includes two or more of the following: a cap, a syringe, a tubing, a medical device connector, or any combination thereof.

Clause 35. The system of any of clauses 32-34, wherein the one or more processors are further programmed and/or configured to determine, based on the sound signature, a subtype of the determined type of the medical device connected to the needleless connector from a plurality of subtypes of that type of medical device.

Clause 36. The system of any of clauses 32-35, wherein the event associated with the needleless connector includes an operation of a medical device connected to the needleless connector, and wherein the one or more processors are further programmed and/or configured to determine, based on the sound signature, a state of the medical device connected to the needleless connector.

Clause 37. The system of any of clauses 32-36, wherein the state of the medical device includes an unused state or a used state.

Clause 38. The system of any of clauses 32-37, wherein the medical device includes a syringe, and wherein the operation of the syringe includes a depression of a plunger of the syringe into a barrel of the syringe, and wherein the depression of the plunger of the syringe into the barrel of the syringe generates the sound signature.

Clause 39. The system of any of clauses 32-38, wherein the plunger of the syringe includes one or more extrusions that generate the sound signature in combination with the barrel of the syringe when the plunger of the syringe is depressed into the barrel of the syringe.

Clause 40. The system of any of clauses 32-39, wherein the state of the medical device includes a volume of fluid expelled from the syringe when the plunger of the syringe is depressed into the barrel of the syringe.

Clause 41. The system of any of clauses 32-40, wherein the medical device includes a disinfectant cap.

Clause 42. The system of any of clauses 32-41, wherein the disinfectant cap includes a switch, and wherein the operation of the disinfectant cap includes a connection of the disinfectant cap to the needleless connector, and wherein connection of the disinfectant cap to the needleless connector generates the sound signature when the state of the disinfectant cap includes the unused state, and wherein, when the state of the disinfectant cap includes the used state, the connection of the disinfectant cap to the needleless connector one of: (i) does not generate the sound signature and (ii) generates another sound signature different than the sound signature generated when the state of the disinfectant cap includes the unused state.

Clause 43. The system of any of clauses 32-42, wherein the switch includes a bi-stable metal dome switch.

Clause 44. A system, comprising: a needleless connector including a fluid flow path and a septum; an optical sensor connected to the needleless connector, wherein the optical sensor is configured to detect a movement of the septum; and one or more processors programmed and/or configured to: receive, from the optical sensor, a signal associated with the movement of the septum; and determine, based on the signal, an event associated with the needleless connector.

Clause 45. The system of clause 44, wherein the event associated with the needleless connector includes at least one of: a connection event in which the needleless connector is connected to a medical device, a disconnection event in which the needleless connector is disconnected from the medical device.

Clause 46. The system of any of clauses 44 and 45, wherein the septum includes one or more markings, and wherein the optical sensor is configured to detect a movement of the one or more markings to detect the movement of the septum.

Clause 47. The system of any of clauses 44-46, wherein the optical sensor is further configured to detect at least one of a color signature and a reflectance of the medical device, and wherein the one or more processors are further programmed and/or configured to determine, based on the at least one of the color signature and the reflectance of the medical device, a type of the medical device.

Clause 48. A system, comprising: a needleless connector including a fluid flow path, wherein the needleless connector is connected to catheter hub of a catheter including a catheter lumen and a needle tip for delivering fluid to a patient at an opposite end of the catheter lumen from the catheter hub; a pressure sensor connected to the needleless connector, wherein the pressure sensor is configured to sense a pressure transmitted through at least one of a fluid in the catheter and a material of the catheter; and one or more processors programmed and/or configured to: receive, from the pressure sensor, a signal associated with the sensed pressure; and determine, based on the signal, an event associated with the catheter.

Clause 49. The system of clause 48, wherein the event associated with the catheter includes a time at which the needle tip of the catheter enters a blood vessel of the patient, and wherein the one or more processors are programmed and/or configured to determine the time at which the needle tip of the catheter enters the blood vessel based on at least one: of a heart rate, a respiration rate, a blood pressure, a penetration force of the needle tip, or any combination thereof, determined from the signal associated with the sensed pressure.

Clause 50. The system of any of clauses 48 and 49, wherein the event associated with the catheter includes a clamping sequence, and wherein the one or more processors are programmed and/or configured to determine the clamping sequence based on one or more changes over time in the signal associated with the sensed pressure.

Clause 51. The system of any of clauses 48-50, wherein the one or more processors are programmed and/or configured to determine, based on the determined clamping sequence and a type of the needleless connector, whether the determined clamping sequence satisfies a clamping protocol associated with the type of the needleless connector.

Clause 52. The system of any of clauses 48-51, wherein the event associated with the catheter includes an occlusion of the catheter lumen, and wherein the one or more processors are programmed and/or configured to determine the occlusion of the catheter lumen based on a rate of change in the sensed pressure.

DETAILED DESCRIPTION

Figure 1:
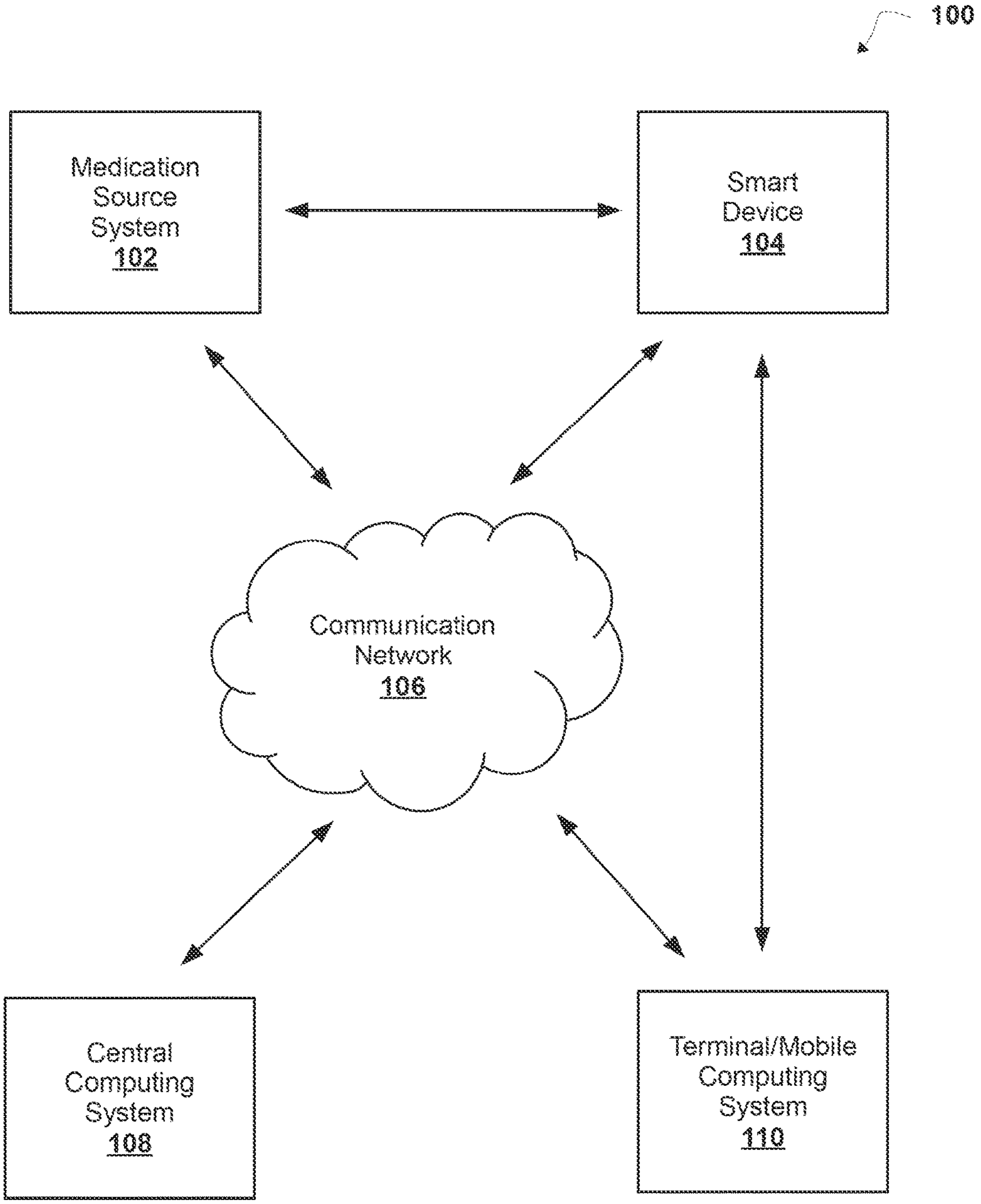
FIG. 1 is a diagram of non-limiting embodiments or aspects of an environment in which systems, devices, products, apparatus, and/or methods, described herein, can be implemented.

It is to be understood that the present disclosure may assume various alternative variations and step sequences, except where expressly specified to the contrary. It is also to be understood that the specific devices and processes illustrated in the attached drawings, and described in the following specification, are simply exemplary and non-limiting embodiments or aspects. Hence, specific dimensions and other physical characteristics related to the embodiments or aspects disclosed herein are not to be considered as limiting.

For purposes of the description hereinafter, the terms "end," "upper," "lower," "right," "left," "vertical," "horizontal," "top," "bottom," "lateral," "longitudinal," and derivatives thereof shall relate to embodiments or aspects as they are oriented in the drawing figures. However, it is to be understood that embodiments or aspects may assume various alternative variations and step sequences, except where expressly specified to the contrary. It is also to be understood that the specific devices and processes illustrated in the attached drawings, and described in the following specification, are simply non-limiting exemplary embodiments or aspects. Hence, specific dimensions and other physical characteristics related to the embodiments or aspects of the embodiments or aspects disclosed herein are not to be considered as limiting unless otherwise indicated.

No aspect, component, element, structure, act, step, function, instruction, and/or the like used herein should be construed as critical or essential unless explicitly described as such. Also, as used herein, the articles "a" and "an" are intended to include one or more items, and may be used interchangeably with "one or more" and "at least one." Furthermore, as used herein, the term "set" is intended to include one or more items (e.g., related items, unrelated items, a combination of related and unrelated items, etc.) and may be used interchangeably with "one or more" or "at least one." Where only one item is intended, the term "one" or similar language is used. Also, as used herein, the terms "has," "have," "having," or the like are intended to be open-ended terms. Further, the phrase "based on" is intended to mean "based at least partially on" unless explicitly stated otherwise.

As used herein, the terms "communication" and "communicate" may refer to the reception, receipt, transmission, transfer, provision, and/or the like of information (e.g., data, signals, messages, instructions, commands, and/or the like). For one unit (e.g., a device, a system, a component of a device or system, combinations thereof, and/or the like) to be in communication with another unit means that the one unit is able to directly or indirectly receive information from and/or transmit information to the other unit. This may refer to a direct or indirect connection that is wired and/or wireless in nature. Additionally, two units may be in communication with each other even though the information transmitted may be modified, processed, relayed, and/or routed between the first and second unit. For example, a first unit may be in communication with a second unit even though the first unit passively receives information and does not actively transmit information to the second unit. As another example, a first unit may be in communication with a second unit if at least one intermediary unit (e.g., a third unit located between the first unit and the second unit) processes information received from the first unit and communicates the processed information to the second unit. In some non-limiting embodiments or aspects, a message may refer to a network packet (e.g., a data packet and/or the like) that includes data. It will be appreciated that numerous other arrangements are possible.

As used herein, the term "computing device" may refer to one or more electronic devices that are configured to directly or indirectly communicate with or over one or more networks. A computing device may be a mobile or portable computing device, a desktop computer, a server, and/or the like. Furthermore, the term "computer" may refer to any computing device that includes the necessary components to receive, process, and output data, and normally includes a display, a processor, a memory, an input device, and a network interface. A "computing system" may include one or more computing devices or computers. An "application" or "application program interface" (API) refers to computer code or other data sorted on a computer-readable medium that may be executed by a processor to facilitate the interaction between software components, such as a client-side front-end and/or server-side back-end for receiving data from the client. An "interface" refers to a generated display, such as one or more graphical user interfaces (GUIs) with which a user may interact, either directly or indirectly (e.g., through a keyboard, mouse, touchscreen, etc.). Further, multiple computers, e.g., servers, or other computerized devices directly or indirectly communicating in the network environment may constitute a "system" or a "computing system".

It will be apparent that systems and/or methods, described herein, can be implemented in different forms of hardware, software, or a combination of hardware and software. The actual specialized control hardware or software code used to implement these systems and/or methods is not limiting of the implementations. Thus, the operation and behavior of the systems and/or methods are described herein without reference to specific software code, it being understood that software and hardware can be designed to implement the systems and/or methods based on the description herein.

Some non-limiting embodiments or aspects are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, etc. In some non-limiting embodiments or aspects, satisfying a threshold may refer to recognition of a pattern in a signal as a result of a pattern recognition technique, a data mining technique, a slope of signal analysis, an Xbar R chart analysis, and/or the like being applied to the signal. For example, satisfying a threshold may be based on a dynamic time based analysis of a signal.

Provided are improved systems, devices, products, apparatus, and/or methods for event monitoring. Existing systems for compliance event monitoring may not incorporate sensors at needleless connectors for use during compliance events. In this way, existing systems for compliance monitoring may have no mechanism to automatically detect scrubbing, flushing, connection events, and/or disconnection events at needleless connectors. Accordingly, existing systems for compliance monitoring may not ensure proper catheter maintenance and/or lead to sub-optimal patient outcomes.

Non-limiting embodiments or aspects of the present disclosure are directed to systems, devices, products, apparatus, and/or methods that use a sensor connected to a needleless connector to obtain a signal. For example, non-limiting embodiments or aspects of the present disclosure are directed to systems, devices, products, apparatus, and/or methods that use a force sensor connected to a needleless connector to obtain a force signal (e.g., a signal indicative of at least one of the following: an instantaneous force, an instantaneous pressure, an instantaneous vibration, a dynamic or changing force over time and/or a moving change in force, a dynamic or changing pressure over time and/or a moving change in force, a dynamic or changing vibration over time and/or a moving change in force, etc.). It is noted herein that the term "force sensor connected to a needleless connector" may mean a force sensor of the present application that is physically coupled to a needleless connector to obtain a force signal. Alternatively, the term "force sensor connected to a needleless connector" may mean a force sensor of the present application that is provided in indirect communication with the needleless connector to obtain a force signal. In such an indirect configuration, the sensor may be adapted to provide a measure of force and/or position and an intermediate coupler may transmit the force and/or position from the needleless connector to the sensor. In some non-limiting embodiments or aspects, a force sensor may include at least one of the following: a force sensor, a piezoelectric element, a force sensitive resistive (FSR) sensor, a strain gauge, a mechanical switch, a flow sensor, a pressure sensor, an acoustic sensor, a microphone, an accelerometer, or any combination thereof.

In some non-limiting embodiments or aspects, a method may include obtaining a signal measured by a sensor connected to a needleless connector including a fluid flow path, determining, based on the signal, at least one of: a scrubbing event in which the needleless connector is scrubbed with a disinfectant, a flushing event in which the needleless connector is flushed with a solution, a connection event in which the needleless connector is connected to a medical device, a disconnection event in which the needleless connector is disconnected from the medical device, or any combination thereof, and providing an indication of the determined event.

In this way, non-limiting embodiments or aspects of the present disclosure provide for more automatic adherence to catheter maintenance protocols and/or more optimal patient outcomes. For example, non-limiting embodiments or aspects of the present disclosure provide for detecting scrubbing, flushing, connection events, and/or disconnection events at a needleless connector, though incorporation of one or more sensors in and/or at the needleless connector, which enables improved tracking of catheter compliance protocols and feedback related thereto, as well as the incorporation of secondary sensors that may indicate location status to improve patient outcomes.

Referring now to FIG. 1, FIG. 1 is a diagram of an example environment 100 in which devices, systems, methods, and/or products described herein, may be implemented. As shown in FIG. 1, environment 100 includes medication source system 102, smart device 104, communication network 106, central computing system 108, and terminal/mobile computing system 110. Systems and/or devices of environment 100 can interconnect via wired connections, wireless connections, or a combination of wired and wireless connections.

In some non-limiting embodiments or aspects, medication source system 102 includes one or more devices capable of delivering one or more fluids to one or more lumens (e.g., fluid lines, IV lines, etc.). For example, medication source system 102 may include one or more manual fluid delivery systems (e.g., one or more IV bags, one or more syringes, etc.) and/or an infusion pump system including one or more infusion pumps. In some non-limiting embodiments, smart device 104 may include a plurality of smart devices 104 (e.g., one or more other and/or differ types of smart devices 104, etc.).

In some non-limiting embodiments or aspects, medication source system 102 includes one or more devices capable of receiving information and/or data from smart device 104, communication network 106, central computing system 108, and/or terminal/mobile computing system 110 and/or communicating information and/or data to smart device 104, communication network 106, central computing system 108, and/or terminal/mobile computing system 110. For example, medication source system 102 may include one or more computing systems including one or more processors (e.g., one or more computing devices, one or more mobile computing devices, etc.).

Further details regarding non-limiting embodiments or aspects of medication source system 102 are provided below with regard to FIGS. 2A, 2C, and 3.

In some non-limiting embodiments or aspects, smart device 104 includes one or more devices capable of receiving information and/or data from medication source system 102, one or more other smart devices 104, communication network 106, central computing system 108, and/or terminal/mobile computing system 110 and/or communicating information and/or data to medication source system 102, one or more other smart devices 104, communication network 106, central computing system 108, and/or terminal/mobile computing system 110. For example, smart device 104 may include one or more computing systems including one or more processors (e.g., one or more computing devices, one or more mobile computing devices, etc.). In some non-limiting embodiments or aspects, smart device 104 may be capable of receiving information (e.g., from medication source system 102 (e.g., from medication source controller 204 and/or from medication source device 206, etc.), from terminal/mobile computing system 110, from one or more other smart devices 104, etc.) via a short range wireless communication connection (e.g., an NEC or proprietary communication connection, an RFID communication connection, a Bluetooth® communication connection, and/or the like), and/or communicating information (e.g., to medication source system 102 (e.g., to medication source controller 204 and/or to medication source device 206, etc.), to terminal/mobile computing system 110, to one or more other smart devices 104, etc.) via a short range wireless communication connection.

Figure 6A:
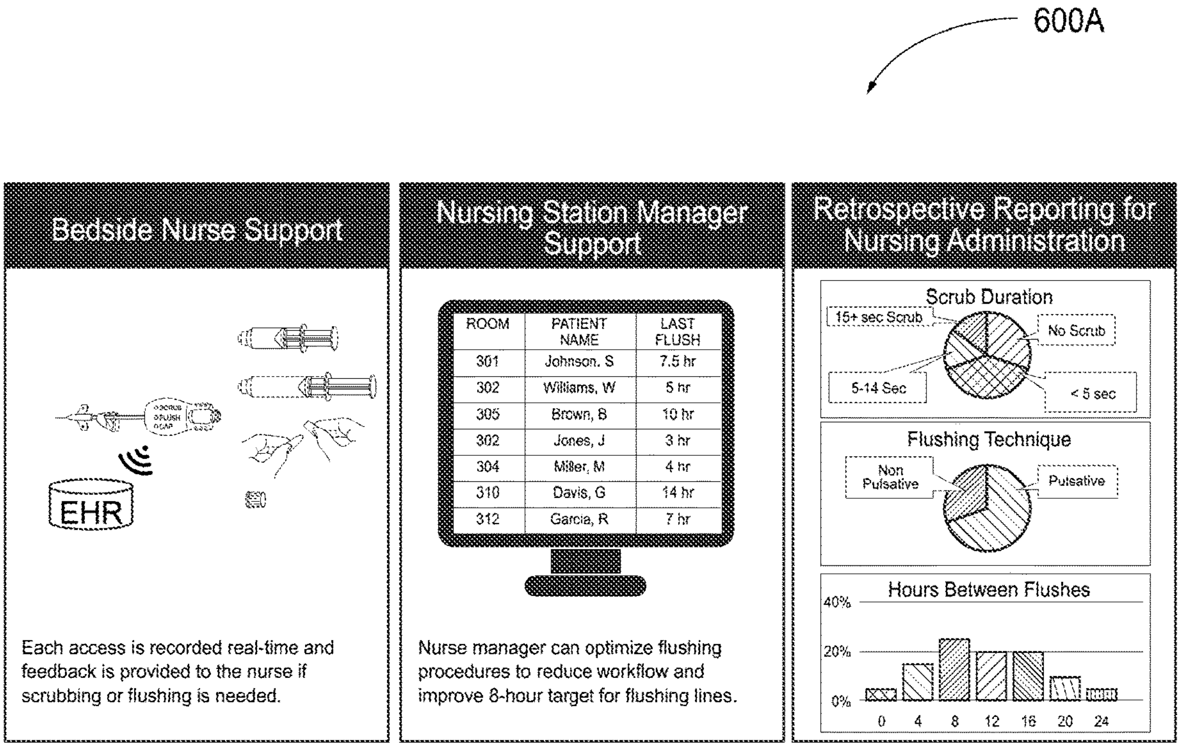
FIGS. 6A and 6B show non-limiting embodiments or aspects of output of one or more systems and/or one or more devices of FIG. 1.
Figure 6B:
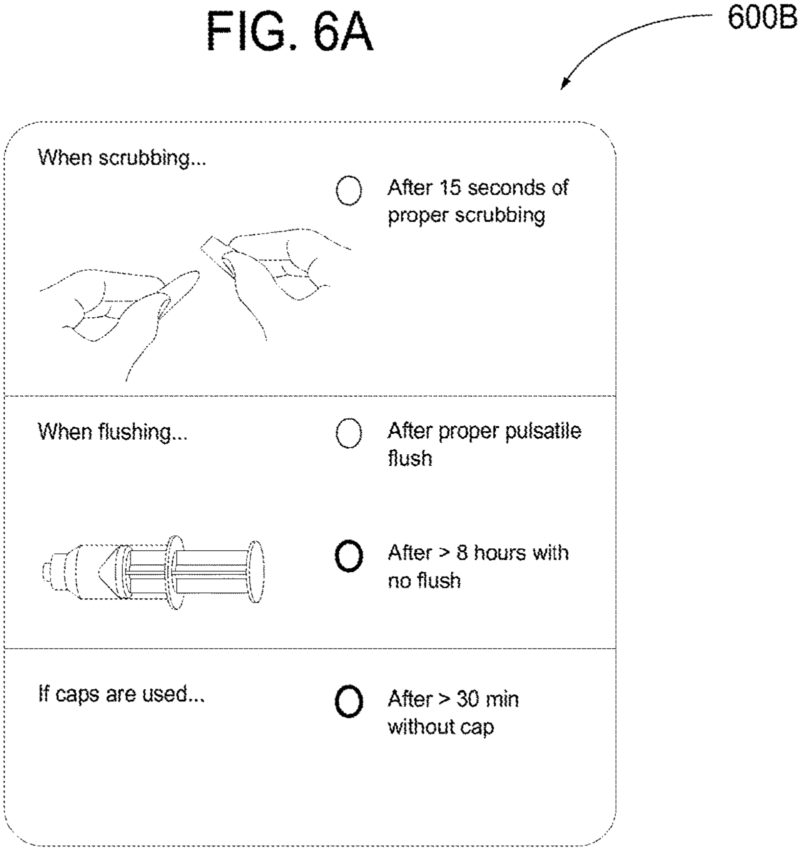

In some non-limiting embodiments or aspects, as shown in FIG. 6B, smart device 104 may provide direct patient-side feedback (e.g., via an LED light to a nurse, etc.) in response to (i) detecting that needleless connector 214 and/or lumen 212 thereof has not been scrubbed for a predetermined period of time and/or before a scheduled use, (ii) detecting that needleless connector 214 and/or lumen 212 thereof has not been scrubbed for a sufficient period of time prior to accessing a catheter line, (iii) detecting that a flush of needleless connector 214 and/or lumen 212 is due, (iv) detecting that a disinfection cap was not attached after a previous access to needleless connector 214 and/or lumen 212, and/or the like. For example, smart device 104 may include needleless connector 214, and needleless connector 214 may be configured to detect at least one of a scrubbing event, a flushing event, a connection or capping event, or any combination thereof. As an example, and needleless connector 214 may be configured to provide information and/or data associated with a detected scrubbing event, a detected flushing event, a detected connection or capping event, and/or a detected disconnection event (e.g., with processor 304, memory 306, storage component 308, input component 310, output component 312, etc.) to store events and report compliance performance for compliance event monitoring.

Further details regarding non-limiting embodiments or aspects of smart device 104 are provided below with regard to FIGS. 2A-2C, 3, 4A-4C, 5A-5C, 6A, 6B, and 7.

In some non-limiting embodiments or aspects, communication network 106 includes one or more wired and/or wireless networks. For example, communication network 106 includes a cellular network (e.g., a long-term evolution (LTE) network, a third generation (3G) network, a fourth generation (4G) network, a code division multiple access (CDMA) network, etc.), a public land mobile network (PLMN), a local area network (LAN), a wide area network (WAN), a metropolitan area network (MAN), a telephone network (e.g., the public switched telephone network (PSTN)), a private network, an ad hoc network, an intranet, the Internet, a fiber optic-based network, a cloud computing network, and/or the like, and/or any combination of these or other types of networks.

In some non-limiting embodiments or aspects, central computing system 108 includes one or more devices capable of receiving information and/or data from medication source system 102, smart device 104, communication network 106, and/or terminal/mobile computing system 110 and/or communicating information and/or data to medication source system 102, smart device 104, communication network 106, and/or terminal/mobile computing system 110. For example, medication source system 102 may include one or more computing systems including one or more processors (e.g., one or more computing devices, one or more mobile computing devices, etc.). In some non-limiting embodiments or aspects, central computing system 108 includes a secure hospital server and/or one or more secure hospital databases that store personally identifiable information (PII) and/or Health Insurance Portability and Accountability Act (HIPAA) protected information.

In some non-limiting embodiments or aspects, terminal/mobile computing system 110 includes one or more devices capable of receiving information and/or data from medication source system 102, smart device 104, communication network 106, and/or central computing system 108 and/or communicating information and/or data to medication source system 102, smart device 104, communication network 106, and/or central computing system 108. For example, terminal/mobile computing system 110 may include one or more computing systems including one or more processors (e.g., one or more computing devices, one or more mobile computing devices, etc.). In some non-limiting embodiments or aspects, terminal/mobile computing system 110 includes a nurse station in a hospital. For example, as shown in an implementation 600A FIG. 6A, terminal/mobile computing system 110 may provide bedside nurse support (e.g., recordation of each access to needleless connector 214 and/or lumen 212 in real-time and feedback to a nurse if scrubbing or flushing is determined to be due or needed according to the recorded access, etc.), nursing station manager support (e.g., optimization of flushing procedures to reduce workflow and improve timed targets for flushing a needleless connector 214 and/or lumen 212, etc.), retrospective reporting for nursing administration (e.g., a scrub duration, a flushing technique, a time between flushes, and/or the like for a needleless connector 214 and/or lumen 212, etc.), and/or the like.

Figure 2A:
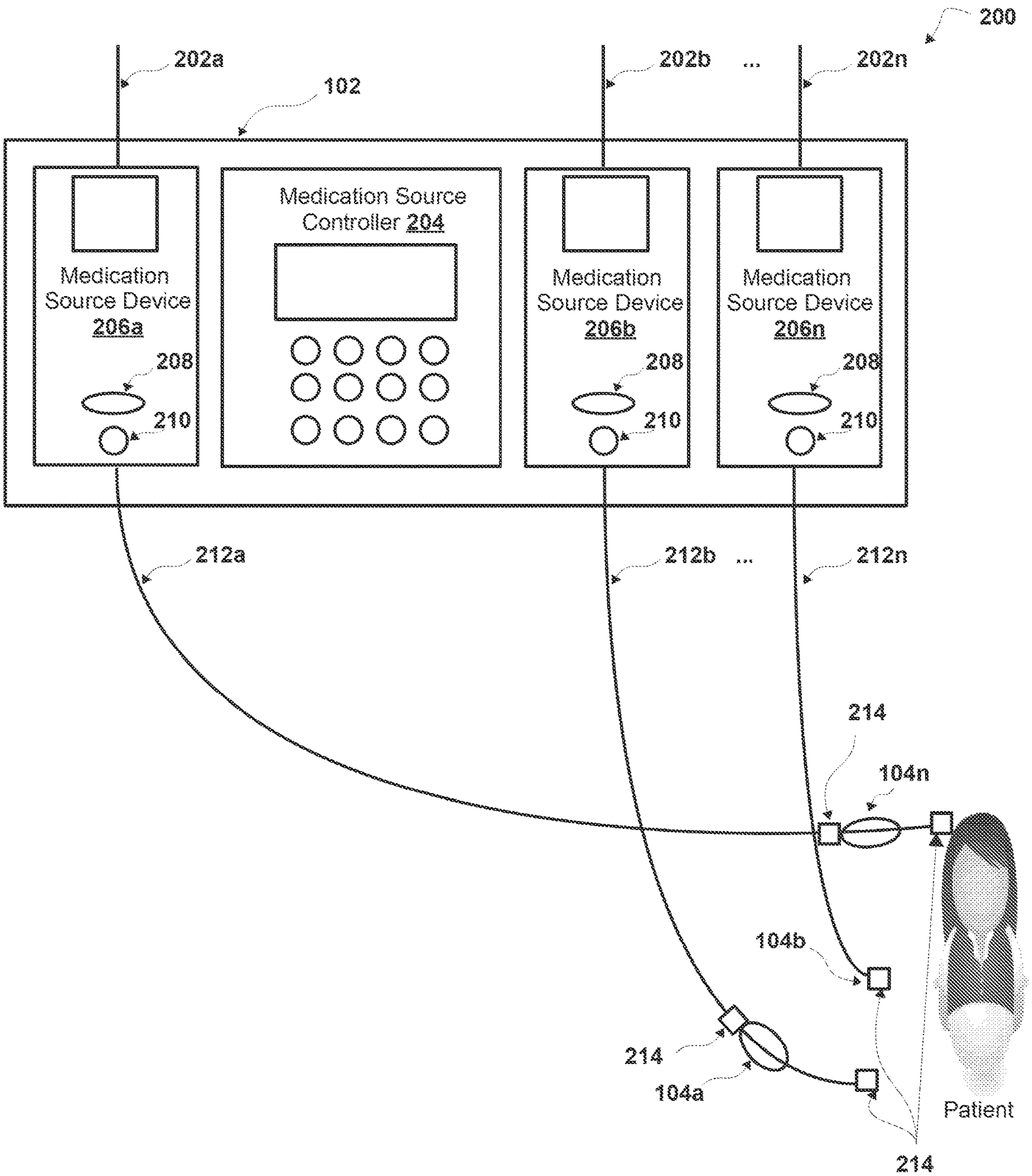
FIGS. 2A-2C are diagrams of non-limiting embodiments or aspects of an implementation of one or more systems and/or one or more devices of FIG. 1.
Figure 2B:
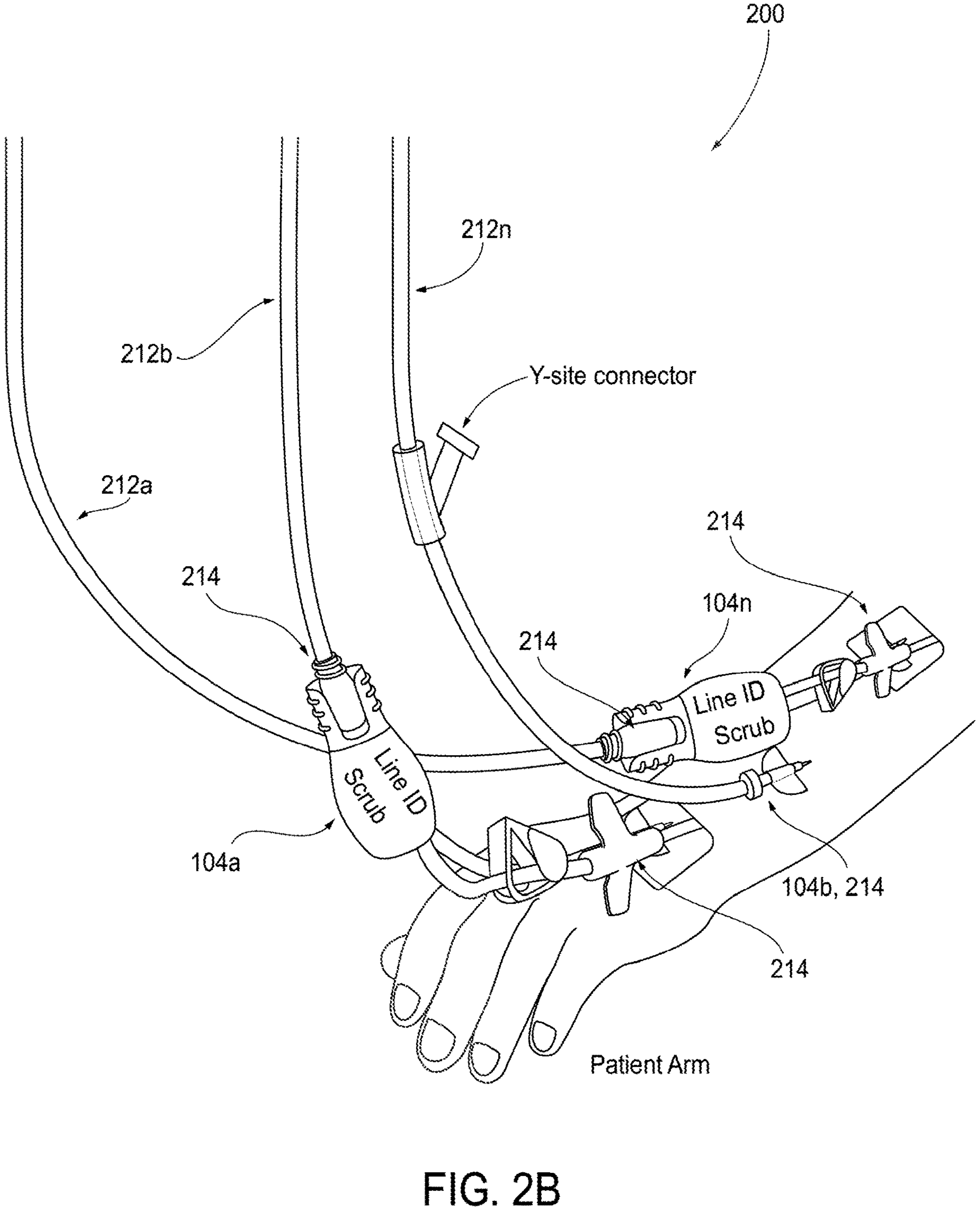
Figure 2C:
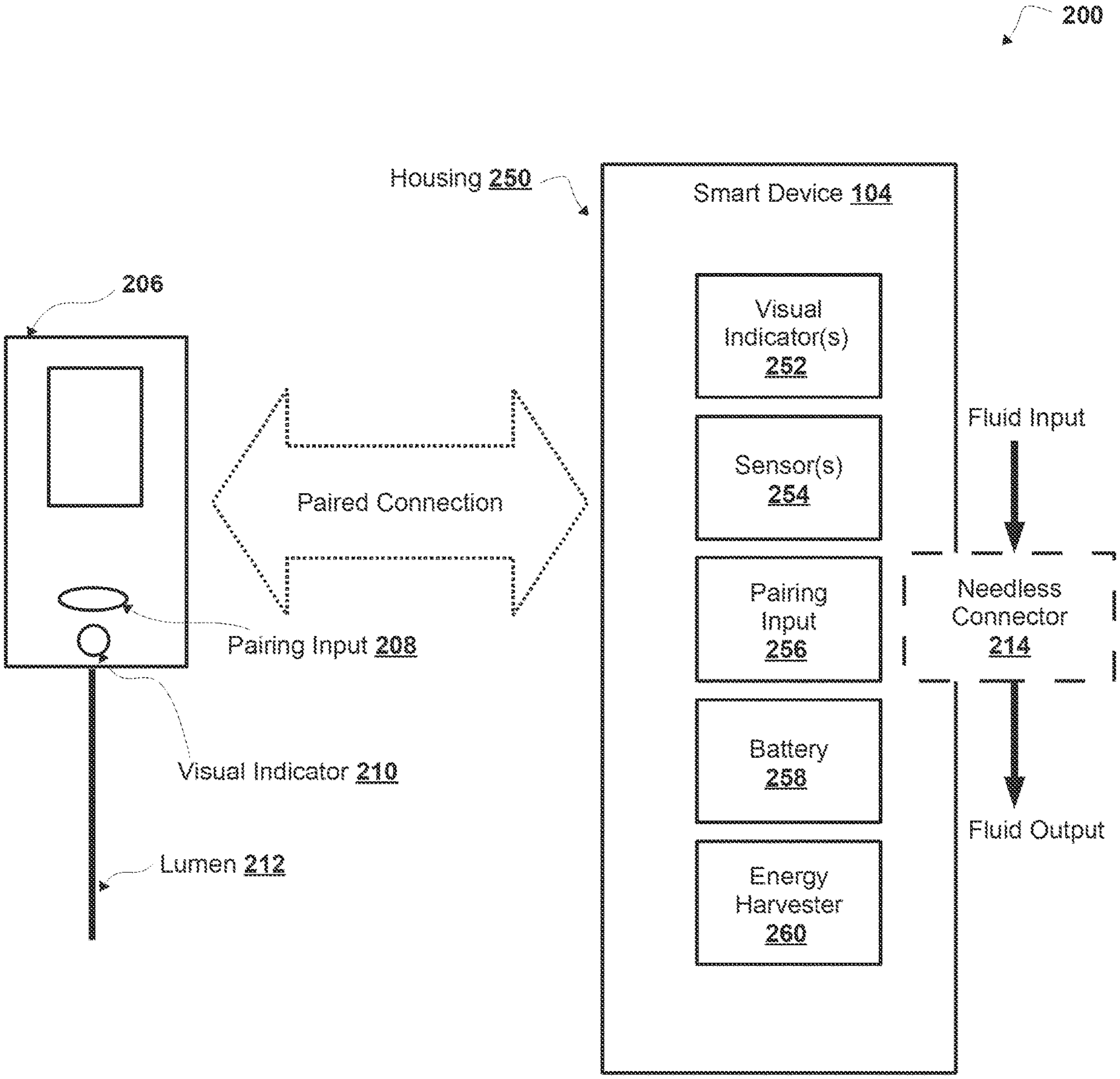

Referring now to FIGS. 2A-2C, FIGS. 2A-2C are diagrams of non-limiting embodiments or aspects of an implementation 200 of one or more systems and/or one or more devices of FIG. 1. As shown in FIGS. 2A and 2C, medication source system 102 may include a medication source controller 204 and/or one or more medication source devices 206 (e.g., a plurality of mediation source devices 206*a*, 206*b*, . . . , 206*n*, etc.). As an example, medication source controller 204 may include an infusion pump controller and/or medication source device 206 may include an infusion pump. In such an example, medication source system 102 may include the BD Alaris™ system. For example, medication source system 102 may include a BD Alaris™ PC Unit and one or more BD Alaris™ Pump Modules. As another example, medication source controller 204 may include a bed-side console or computing device, which may be separate from an infusion pump system, and/or medication source device 206, which may be separate from an infusion pump, may be associated with and/or connected to a medication source (e.g., an IV bag, a syringe, an end of an IV line connected and proximal to an IV bag or a syringe, etc.).

As shown in FIG. 2A, the plurality of medication source devices 206*a*, 206*b*, . . . 206*n* may be connected to a plurality of lumens (e.g., fluid lines, etc.) 202*a*, 202*b*, . . . 202*n* (e.g., for receiving a fluid and/or a medication at medication source system 102) and/or a plurality of lumens (e.g., fluid lines, etc.) 212*a*, 212*b*, . . . 212*n* (e.g., for delivering a fluid and/or a medication from medication source system 102, etc.). As shown in FIG. 2C, medication source device 206 may include pairing input 208 (e.g., a button, input component 310, etc.) and/or visual indicator 210 (e.g., a multi-color LED(s), output component 312, etc.). As shown in FIGS. 2A and 2B, the plurality of lumens 212*a*, 212*b*, . . . 212*n* may be connected to a plurality of smart devices 104*a*, 104*b*, . . . 104*n*.

In some non-limiting embodiments or aspects, smart device 104 is configured to be removably connected to needleless connector 214 and/or a portion of lumen 212 proximate needleless connector 214, such as an IV lumen (e.g., a peripherally inserted central catheter (PICC), a peripheral intravenous catheter (PIVC), a central venous catheter (CVC), etc.), and/or the like. For example, smart device 104 may include a clamp, an adhesive, a frictional fit, and/or other attachment means configured to removably connect smart device 104 to needleless connector 214 and/or lumen 212 proximate needleless connector 214. As an example, as shown in FIGS. 2A and 2B, smart device 104*a* may be connected to needleless connector 214 and/or a catheter lumen that connects a catheter to lumen 212*b*, and/or smart device 104*n* may be connected to needleless connector 214 and/or a catheter lumen that connects a catheter to lumen 212*a*. In some non-limiting embodiments or aspects, smart device 104 includes needleless connector 214. For example, smart device 104 may be integrated with needleless connector 214 (e.g., within needleless connector 214 and/or within a catheter hub of a needleless connector of a fluid invasive device, etc.). As an example, as shown in FIGS. 2A and 2B, smart device 104*b* may include needleless connector 214 and/or a catheter hub that connects a catheter lumen to lumen 212*n* via a Y-site connector. In such an example, smart device 104 may include needleless connector 214 including housing 402 of needleless connector 214 within housing 250 (e.g., integrated with housing 250, encompassed within housing 250, etc.). For example, needleless connector 214 may embed housing 250, smart device 104, and/or components thereof within housing 402 of needleless connector 214 (or vice-versa) or housing 250, smart device 104, and/or components thereof connected to housing 402. An advantage of adding sensors to standard designs is that the clinically validated performance characteristics and regulatory filings do not change. Sterilization techniques that are optimum for fluid-path components, may not be ideal for electronic devices and, therefore, therefore designs that do not change validated components that can be added later in manufacturing and assembly, or snapped on by the end-user, may have advantages.

Figure 4A:
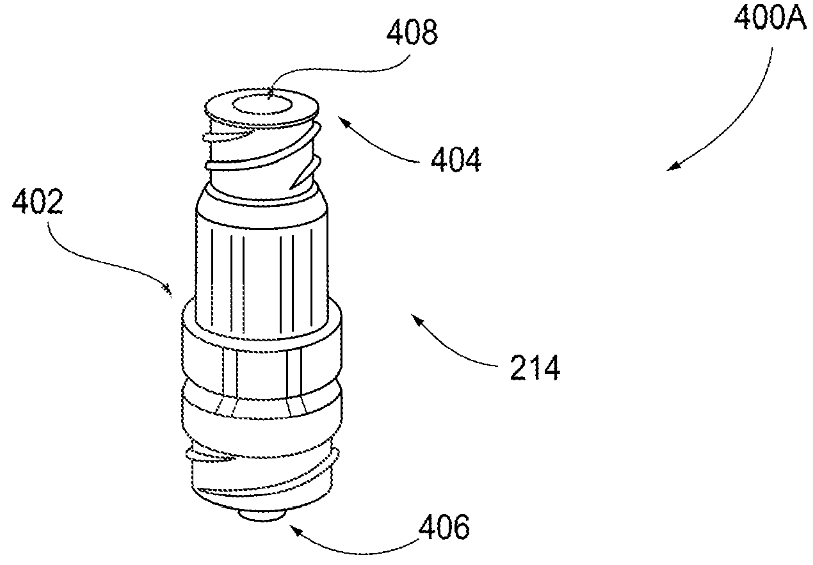
FIG. 4A is a side view of non-limiting embodiments or aspects of an implementation of a needleless connector.
Figure 4B:
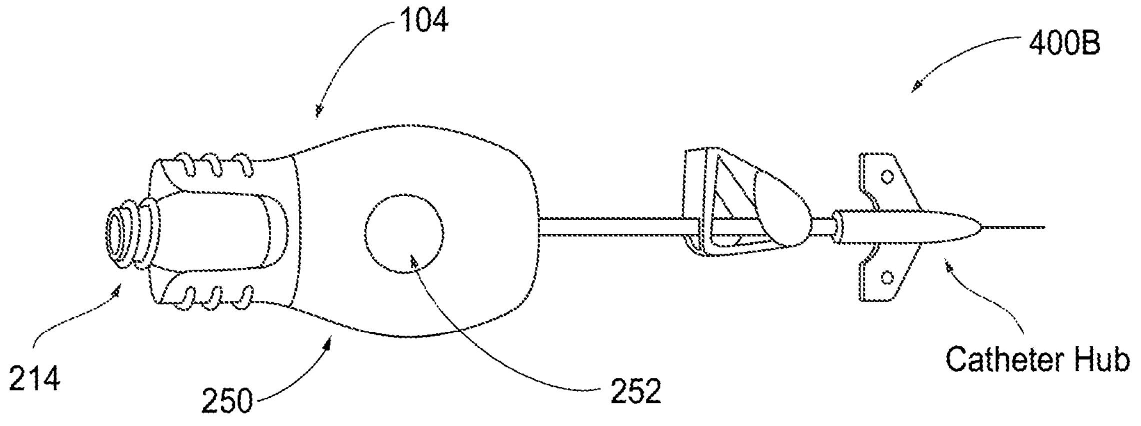
FIG. 4B is a side view of non-limiting embodiments or aspects of an implementation of a smart device and a needleless connector.
Figure 4C:
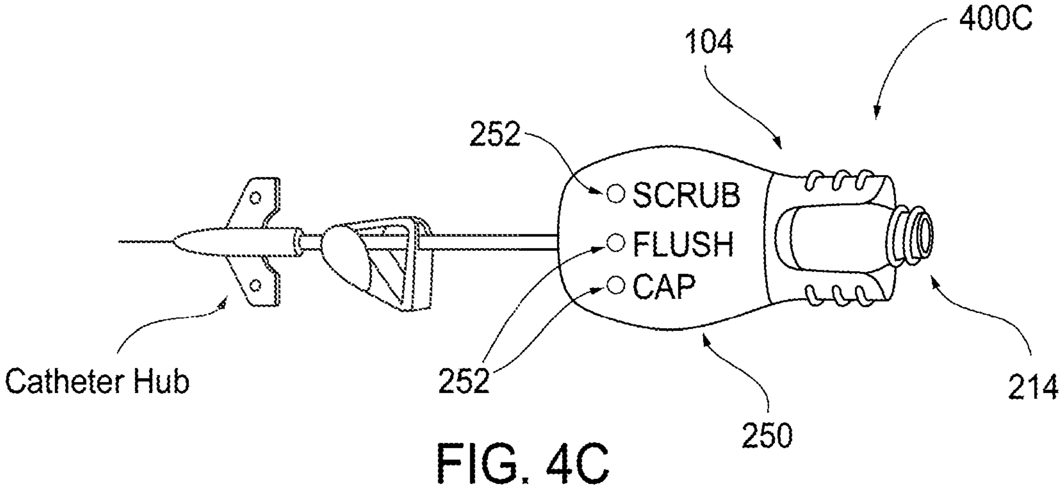
FIG. 4C is a side view of non-limiting embodiments or aspects of an implementation of a smart device and a needleless connector.

Referring also to FIG. 4A, FIG. 4A is a side view of non-limiting embodiments or aspects of an implementation 400A of a needleless connector 214. As shown in FIG. 4A, a needleless connector 214 may include a fluid flow path in a housing 402 between an inlet 404 and an outlet 406 opposite the inlet 404. Inlet 404 may be fluidically sealed by a displaceable septum 408 configured to be displaced to open or connect inlet 404 to the fluid flow path in response to connection of needleless connector 214 to a medical device (e.g., an infusion pump, an IV bag, a syringe, an IV line, etc.). For example, the needleless connector 214 may include the BD MaxPlus™ connector, the BD MaxZero™ needle-free connector, and/or the like. However, non-limiting embodiments or aspects are not limited thereto, and the needleless connector 214 may include any needleless connector 214 for use in fluid administration. For example, needleless connector 214 may include a port, a manifold, a stopcock, an open connector, a leer connector, and/or any other connector that does not rely on (but may or may not include) a needle to form a connection with a device and/or a patient. In some non-limiting embodiments or aspects, one or more components of smart device 104 may be included within housing 402 of needleless connector 214. For example, housing 402 of needleless connector 214 may include housing 250 of smart device 104 (e.g., housing 250 may be integrated with housing 402, encompassed within housing 402, etc.).

As shown in FIG. 2C, smart device 104 may include visual indicator 252 (e.g., one or more visual indicators, a plurality of visual indicators, a multi-color LED(s), a plurality of LEDs, output component 312, etc.), sensor 254 (e.g., one or more sensors, a plurality of sensors, a sensor suite, etc.), pairing input 256 (e.g., one or more buttons, one or more force sensors, one or more accelerometers, input component 310, etc.), battery 258, and/or energy harvester 260 (e.g., a thermoelectric energy harvester, a photovoltaic energy harvester, a piezoelectric energy harvester, etc.). Visual indicator 252, sensor 254, pairing input 256, battery 258, energy harvester 260 and all or a portion of needleless connector 214 may be included within housing 250 of smart device 104. Visual indicator 252 may be visible through and/or extend from a sidewall of housing 250. Battery 258 and/or energy harvester 260 may provide power for operating components of smart device 104, such as visual indicator 252, sensor 254, pairing input 256, a rechargeable battery of battery 258, one or more components of device 300 included in smart device 104, and/or the like.

In some non-limiting embodiments or aspects, smart device 104 may include a label (e.g., a human readable label, etc.) that characterizes visual indicator 252 of smart device 104. For example, as shown in implementation 400C in FIG. 4C, smart device 104 may include labels associated with visual indicators 252 (e.g., on a sidewall of housing 250, etc.) that characterize each visual indicator 252 as configured for providing an indication associated a particular event, such as one of: a scrubbing event in which needleless connector 214 is scrubbed with a disinfectant (e.g., a label "SCRUB", etc.); a flushing event in which needleless connector 214 is flushed with a solution (e.g., a label "FLUSH", etc.); a connection or capping event in which needleless connector 214 is connected to a medical device (e.g., a label "CAP", etc.); and/or the like. In some non-limiting embodiments or aspects, smart device 104 may include a single visual indicator 252 (e.g., as shown in implementation 400B in FIG. 4B). For example, smart device 104 may control single visual indicator 252 to illuminate in a particular color and/or in a particular pattern to provide an indication or prompt to a user, such as to illuminate a continuous green in response to sensing that scrubbing of needleless connector 214 has occurred for a predetermined period of time (e.g., 15 seconds, etc.), to illuminate a pulsating green in response to sensing that a proper pulsatile flush has occurred, to illuminate a pulsating red in response to determining that a pulsatile flush of needleless connector 214 has not occurred for a predetermined period of time (e.g., 88 hours, etc.), to illuminate a continuous red in response to determining that needleless connector 214 has not been capped with a disinfectant cap for a predetermined period of time (e.g., over minutes, etc.)

In some non-limiting embodiments or aspects, communication circuitry (e.g., communication interface 314, etc.) of medication source device 206 is configured to establish communication with communication circuitry (e.g., communication interface 314, etc.) of smart device 104 based on user input to pairing input 208 of medication source device 206 and user input to pairing input 256 of smart device 104. For example, medication source device 206 may establish a short range wireless communication connection (e.g., an NFC communication connection, an RFID communication connection, a Bluetooth® communication connection, etc.) with smart device 104. As an example, visual indicator 210 may be configured to emit a predetermined light pattern (e.g., to blink rapidly to indicate that medication source device 206 is in a pairing mode, etc.) in response to a predetermined user input to pairing input 208 (e.g., in response to a user pressing and holding a button of pairing input 208, etc.) of medication source device 206. In such an example, smart device 104 may be configured to establish communication with medication source device 206 (e.g., pair and/or activate a pairing sequence for pairing smart device 104 with medication source device 206, etc.) in response to a predetermined user input to paring input 256 (e.g., in response to a user pressing and holding a button of pairing input 256, etc.) of smart device 104 at a same time that medication source device 206 is in the pairing mode.

In some non-limiting embodiments or aspects, when medication source device 206 is paired with smart device 104, visual indicator 210 of medication source device 206 and visual indicator 252 of smart device 104 are configured to provide a same type of visual output (e.g., a same color of light from a multi-colored LED, a same pattern of light, etc.). For example, and referring again to FIG. 2A, medication source device **206*a* may be paired with smart device 104*n* and each of medication source device 206*a* and smart device 104*n* may output a first color of light (e.g., red light), medication source device 206*b* may be paired with smart device 104*a* and each of medication source device 206*b* and smart device 104*a* may output a second color of light (e.g., green light), medication source device 206*n* may be paired with smart device 104*b* and each of medication source device 206*n* and smart device 104*b*** may output a third color of light (e.g., blue light), and/or the like.

In some non-limiting embodiments or aspects, sensor 254 includes at least one of: one or more force sensors (e.g., one or more piezoelectric elements or transducers, one or more force sensitive resistive (FSR) sensors, one or more strain gauges, etc.); one or more accelerometers; one or more gyroscopes; one or more pressure sensors; one or more acoustic sensors (e.g., an acoustic sensor configured to detect a sound signature associated with a type, a state, and/or an operation of a medical device, etc.); one or more optical sensors (e.g., an optical sensor configured to detect at least one of a movement of a septum, a color signature and a reflectance of a medical device connected to smart device 104, etc.), one or more identification sensors (e.g., an identification sensor configured to detect an identification tag on a medical device connected to or being connected to the needleless connector 214, such as a magnetometer configured to detect a magnetic material, a barcode scanner configured to read a bar code, etc.); one or more position sensors (e.g., a position sensor configured to detect movement of smart device 104, etc.); one or more RBG color sensors; one or more mechanical switches; one or more flow sensors (e.g., an ultrasonic flow sensor, a thermal flow sensor, etc.); or any combination thereof.

The number and arrangement of systems, devices, and networks shown in FIGS. 1 and 2A-2C are provided as an example. There can be additional systems, devices and/or networks, fewer systems, devices, and/or networks, different systems, devices, and/or networks, or differently arranged systems, devices, and/or networks than those shown in FIGS. 1 and 2A-2C. Furthermore, two or more systems or devices shown in FIGS. 1 and 2A-C can be implemented within a single system or a single device, or a single system or a single device shown in FIGS. 1 and 2A-2C can be implemented as multiple, distributed systems or devices. Additionally, or alternatively, a set of systems or a set of devices (e.g., one or more systems, one or more devices, etc.) of environment 100 and/or implementation 200 can perform one or more functions described as being performed by another set of systems or another set of devices of environment 100 and/or implementation 200.

Figure 3:
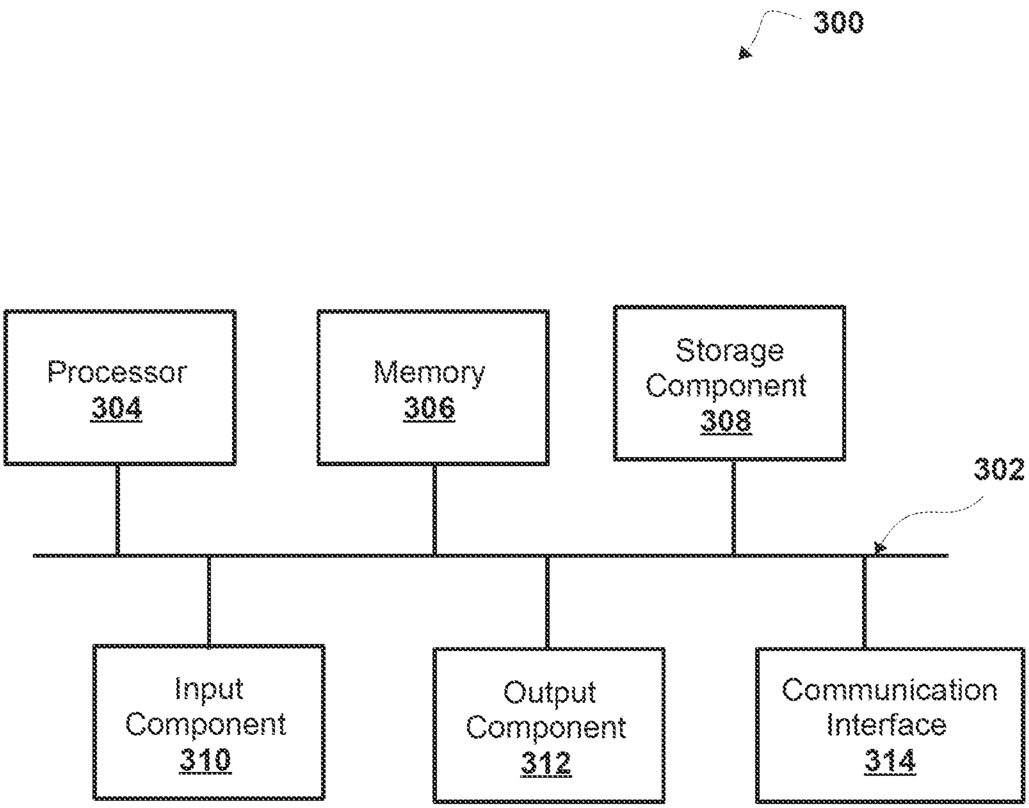
FIG. 3 is a diagram of non-limiting embodiments or aspects of components of one or more devices and/or one or more systems of FIGS. 1 and 2A-2C.

Referring now to FIG. 3, FIG. 3 is a diagram of example components of a device 300. Device 300 may correspond to one or more devices of medication source system 102, smart device 104, and/or one or more devices of communication network 106, one or more devices of central computing system 108, one or more devices of terminal/mobile computing system 110, one or more devices of medication source controller 204, and/or one or more devices of medication source device 206. In some non-limiting embodiments or aspects, one or more devices of medication source system 102, smart device 104, and/or one or more devices of communication network 106, one or more devices of central computing system 108, one or more devices of terminal/mobile computing system 110, one or more devices of medication source controller 204, and/or one or more devices of medication source device 206 can include at least one device 300 and/or at least one component of device 300. As shown in FIG. 3, device 300 may include a bus 302, a processor 304, memory 306, a storage component 308, an input component 310, an output component 312, and a communication interface 314.

Bus 302 may include a component that permits communication among the components of device 300. In some non-limiting embodiments or aspects, processor 304 may be implemented in hardware, firmware, or a combination of hardware and software. For example, processor 304 may include a processor (e.g., a central processing unit (CPU), a graphics processing unit (GPU), an accelerated processing unit (APU), etc.), a microprocessor, a digital signal processor (DSP), and/or any processing component (e.g., a field-programmable gate array (FPGA), an application-specific integrated circuit (ASIC), a microcontroller (MCU), etc.) that can be programmed to perform a function. Memory 306 may include random access memory (RAM), read only memory (ROM), and/or another type of dynamic or static storage device (e.g., flash memory, magnetic memory, optical memory, etc.) that stores information and/or instructions for use by processor 304.

Storage component 308 may store information and/or software related to the operation and use of device 300. For example, storage component 308 may include a hard disk (e.g., a magnetic disk, an optical disk, a magneto-optic disk, a solid state disk, etc.), a compact disc (CD), a digital versatile disc (DVD), a floppy disk, a cartridge, a magnetic tape, and/or another type of computer-readable medium, along with a corresponding drive.

Input component 310 may include a component that permits device 300 to receive information, such as via user input (e.g., a touch screen display, a keyboard, a keypad, a mouse, a button, a switch, a microphone, a camera, an electroencephalogram (EEG) monitor, patient monitoring system etc.). Additionally, or alternatively, input component 310 may include a sensor for sensing information (e.g., a global positioning system (GPS) component, an accelerometer, a gyroscope, an actuator, etc.). Output component 312 may include a component that provides output information from device 300 (e.g., a display, a speaker, one or more light-emitting diodes (LEDs), and/or the like).

Communication interface 314 may include a transceiver-like component (e.g., a transceiver, a separate receiver and transmitter, etc.) that enables device 300 to communicate with other devices, such as via a wired connection, a wireless connection, or a combination of wired and wireless connections. Communication interface 314 may permit device 300 to receive information from another device and/or provide information to another device. For example, communication interface 314 may include an Ethernet interface, an optical interface, a coaxial interface, an infrared interface, a radio frequency (RF) interface, a universal serial bus (USB) interface, a Wi-Fi® interface, a cellular network interface, and/or the like.

Device 300 may perform one or more processes described herein. Device 300 may perform these processes based on processor 304 executing software instructions stored by a computer-readable medium, such as memory 306 and/or storage component 308. A computer-readable medium (e.g., a non-transitory computer-readable medium) is defined herein as a non-transitory memory device. A non-transitory memory device includes memory space located inside of a single physical storage device or memory space spread across multiple physical storage devices.

Software instructions may be read into memory 306 and/or storage component 308 from another computer-readable medium or from another device via communication interface 314. When executed, software instructions stored in memory 306 and/or storage component 308 may cause processor 304 to perform one or more processes described herein. Additionally or alternatively, hardwired circuitry may be used in place of or in combination with software instructions to perform one or more processes described herein. Thus, embodiments or aspects described herein are not limited to any specific combination of hardware circuitry and software.

Memory 306 and/or storage component 308 may include data storage or one or more data structures (e.g., a database, etc.). Device 300 may be capable of receiving information from, storing information in, communicating information to, or searching information stored in the data storage or one or more data structures in memory 306 and/or storage component 308. For example, the information may input data, output data, medical data, or any combination thereof.

The number and arrangement of components shown in FIG. 3 are provided as an example. In some non-limiting embodiments or aspects, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 5A:
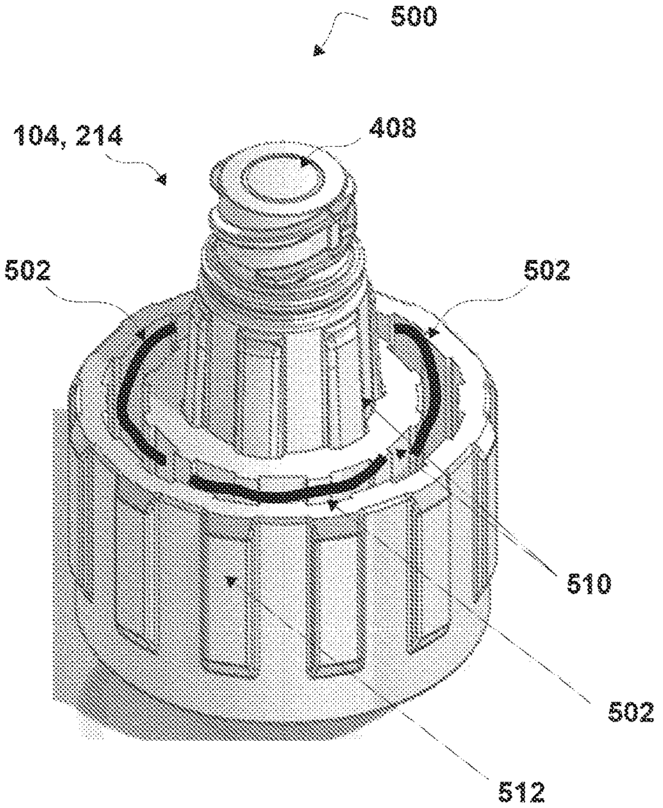
FIG. 5A is a perspective view of non-limiting embodiments or aspects of an implementation of a smart device and a needleless connector.
Figure 5B:
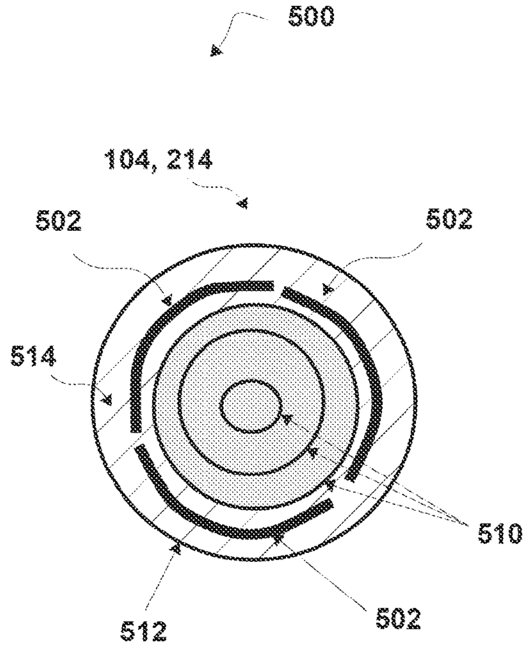
FIG. 5B is a top view of non-limiting embodiments or aspects of an implementation of a smart device and a needleless connector.
Figure 5C:
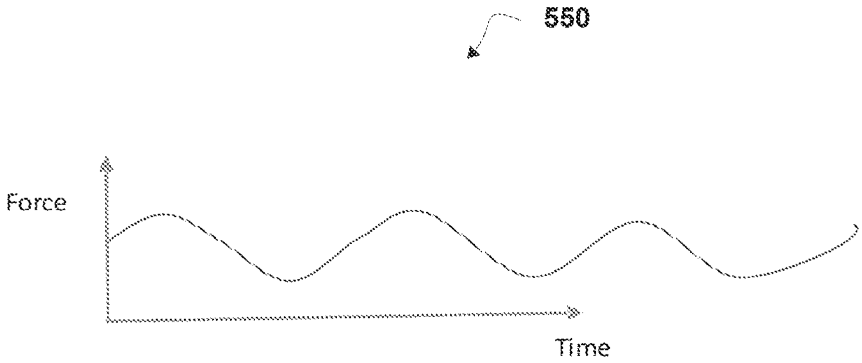
FIG. 5C is a graph of non-limiting embodiments or aspects of a force signal over time.

FIG. 5A is a perspective view and FIG. 5B is a top view of non-limiting embodiments or aspects of an implementation 500 of smart device 104 including needleless connector 214. Referring also to FIG. 4A, needleless connector 214 may include a fluid flow path in housing 402 between inlet 404 and outlet 406 opposite the inlet 404. Inlet 404 may be fluidically sealed by displaceable septum 408 configured to be displaced to open or connect inlet 404 to the fluid flow path in response to connection of needleless connector 214 to a medical device (e.g., an infusion pump, an IV bag, a syringe, an IV line, etc.). Referring again to FIGS. 5A and 5B, in some non-limiting embodiments, smart device 104 may include sensor 254. For example, sensor 254 may include force sensor 502 connected to needleless connector 214. As an example, force sensor 502 may be configured to sense, detect, and/or determine a force signal. In such an example, at least one of: a scrubbing event in which the needleless connector is scrubbed with a disinfectant, a flushing event in which the needleless connector is flushed with a solution, a connection event in which the needleless connector is connected to a medical device, a disconnection event in which the needleless connector is disconnected from the medical device, or any combination thereof, may be determined based on the force signal (e.g., by smart device 104, etc.). In such an example, a pattern of events including a plurality of the least one of: the scrubbing event in which the needleless connector is scrubbed with the disinfectant, the flushing event in which the needleless connector is flushed with the solution, the connection event in which the needleless connector is connected to the medical device, the disconnection event in which the needleless connector is disconnected from the medical device, a time between one or more detected events (e.g., a dwell or connection time during which the needleless connector is connected to medical device between a connection event and a disconnection event, etc.), or any combination thereof may be determined based on the force signal, and a medication administration event in which a medication is administered to a patient via needleless connector 214 may be determined based on the pattern of events. As an example, a standard medical practice may assume a Scrub-Flush-Scrub-MedAdmin-Scrub-Flush-Scrub pattern or sequence of events and, therefore, detection of three access of luer connectors may be interpreted by smart device 104 as a medication administration event. For example, FIG. 5C is a graph 550 of non-limiting embodiments or aspects of a force measurement or signal over time. As shown in FIG. FIG. 5C, pulsatile flushing may be determined or detected by force measurement, for example, when flushing is achieved by intermittent pressure pulses applied to a plunger of a flush syringe, and smart device 104 can detect occurrences of pulsatile flushes by identifying periodic force signals between x-y Hz in a force signal perpendicular to a surface of septum 408 of needleless connector 214. For example, smart device 104 may determine, based on the force signal indicating periodic forces in the second direction perpendicular to the surface of the septum facing in the first direction, the flushing event, and that the flushing event includes a pulsatile flushing event.

In some non-limiting embodiment or aspects, smart device may 104 may include communication circuitry configured to transmit the force signal to a remote computing system. For example, medication source system 102, central computing system 108, and/or terminal/mobile computing system 110 may obtain the force signal from smart device 104 and/or needleless connector 214 and process the force signal to determine at least one of: a scrubbing event in which the needleless connector is scrubbed with a disinfectant, a flushing event in which the needleless connector is flushed with a solution, a connection event in which the needleless connector is connected to a medical device, a disconnection event in which the needleless connector is disconnected from the medical device, or any combination thereof.

In some non-limiting embodiments or aspects, force sensor 502 includes at least one of: a piezoelectric element, a force sensitive resistive (FSR) sensor, a strain gauge, or any combination thereof. In some non-limiting embodiments or aspects, force sensor 502 is positioned between an outer surface of inner wall 510 (e.g., an inner harder plastic wall) of needleless connector 214 defining the fluid flow path of needleless connector 214 and an inner surface of an outer wall 512 (e.g., a softer, a more flexible, a more pliable, a rubber, etc. wall) of needleless connector 214 surrounding the inner wall 510 of needleless connector 214. In some non-limiting embodiments or aspects, an area between an outer surface of inner wall 510 (e.g., an inner harder plastic wall) of needleless connector 214 defining the fluid flow path of needleless connector 214 and an inner surface of an outer wall 512 (e.g., a softer, a more flexible, more, a more pliable, a rubber, etc. wall) of needleless connector 214 surrounding the inner wall 510 of needleless connector 214, which may be held by a user during cleaning and/or connection to another medical device, may be filled with a rubber or other pliable type material 514 including force sensors 502 as force sensing films within the material 514 between the inner wall 510 and the outer wall 512. In some non-limiting embodiments or aspects, force sensors 502 may be located between inner wall 510 and outer wall 512 below threading on and/or proximal to inlet 404 of needleless connector 214.

In some non-limiting embodiments or aspects, force sensor 502 includes a plurality of force sensors 502 positioned around the fluid flow path of needleless connector 214 between the outer surface of inner wall 510 of needleless connector 214 defining the fluid flow path of needleless connector 214 and the inner surface of outer wall 512 of needleless connector 214 surrounding inner wall 510 of needleless connector 214. For example, inlet 404 of needleless connector 214 may include septum 408 including a surface facing in a first direction, and force sensor 502 may be configured to detect a force in a second direction perpendicular to the surface of the septum facing in the first direction. As an example, the flushing event, which may include a pulsatile flushing event, may be determined based on the force signal indicating periodic forces in the second direction perpendicular to the surface of the septum facing in the first direction.

In some non-limiting embodiments or aspects, sensor 254 includes a pressure sensor, and the pressure sensor is one of: in direct contact with a fluid in the fluid flow path of the needleless connector; located within an inner wall of the needleless connector defining the fluid flow path of the needleless connector, and located within a wall of a lumen connected to the needleless connector. For example, smart device 104 may determine or detect pulsatile flush, a flush, and or a med-administration by the pressure sensor in contact with the fluid path in the needleless connector 214 and/or a lumen thereof.

In some non-limiting embodiments or aspects, sensor 254 includes an optical sensor configured to detect at least one of a color signature and a reflectance of a medical device connected to and/or being connected to needleless connector 214, and smart device 104 may determine a type of the medical device based on the at least one of the color signature and the reflectance of the medical device. For example, a color signature and/or the reflectance of the medical device may be indicative of a syringe, an IV bag, an infusion pump, and/or a particular type thereof.

In some non-limiting embodiments or aspects, sensor 254 includes an identification sensor configured to detect an identification tag on a medical device connected to or being connected to the needleless connector. For example, the identification sensor may include a magnetometer, and the identification tag may include a magnetic material on and/or integrated with needleless connector 214.

In some non-limiting embodiments or aspects, sensor 254 includes a position sensor configured to detect movement of the needleless connector. For example, a movement of the patient, a fall event of the patient, a movement of a bed of the patient may be determined (e.g., by smart device 104, etc.) based on the detected movement of the needleless connector.

In some non-limiting embodiments or aspects, sensor 254 includes an RGB color sensor configured to detect a color of a fluid in the fluid flow path of the needleless connector. For example, at least one of a blood-draw in the needleless connector and a retention of blood in the needleless connector may be determined (e.g., by smart device 104, etc.) based on the color of the fluid detected in the fluid flow path of the needleless connector.

In some non-limiting embodiments or aspects, smart device 104 including needleless connector 214 may include visual indicator 252, and visual indicator 252 may be configured to provide a visual indication associated with the at least one of: the scrubbing event in which the needleless connector is scrubbed with the disinfectant, the flushing event in which the needleless connector is flushed with the solution, the connection event in which the needleless connector is connected to the medical device, the disconnection event in which the needleless connector is disconnected from the medical device, or any combination thereof. For example, as shown in an implementation 600B in FIG. 6B, smart device 104 may provide direct patient-side feedback (e.g., via an LED light to a nurse, etc.) in response to (i) detecting that needleless connector 214 and/or lumen 212 thereof has not been scrubbed for a predetermined period of time and/or before a scheduled use, (ii) detecting that needleless connector 214 and/or lumen 212 thereof has not been scrubbed for a sufficient period of time prior to accessing a catheter line, (iii) detecting that a flush of needleless connector 214 and/or lumen 212 is due, (iv) detecting that a disinfection cap was not attached after a previous access to needleless connector 214 and/or lumen 212, and/or the like. For example, smart device 104 may include needleless connector 214, and needleless connector 214 may be configured to detect at least one of a scrubbing event, a flushing event, a connection or capping event, or any combination thereof. As an example, and needleless connector 214 may be configured to provide information and/or data associated with a detected scrubbing event, a detected flushing event, and/or a detected connection or capping event (e.g., with processor 304, memory 306, storage component 308, input component 310, output component 312, etc.) to store events and report compliance performance for compliance event monitoring.

Figure 7:
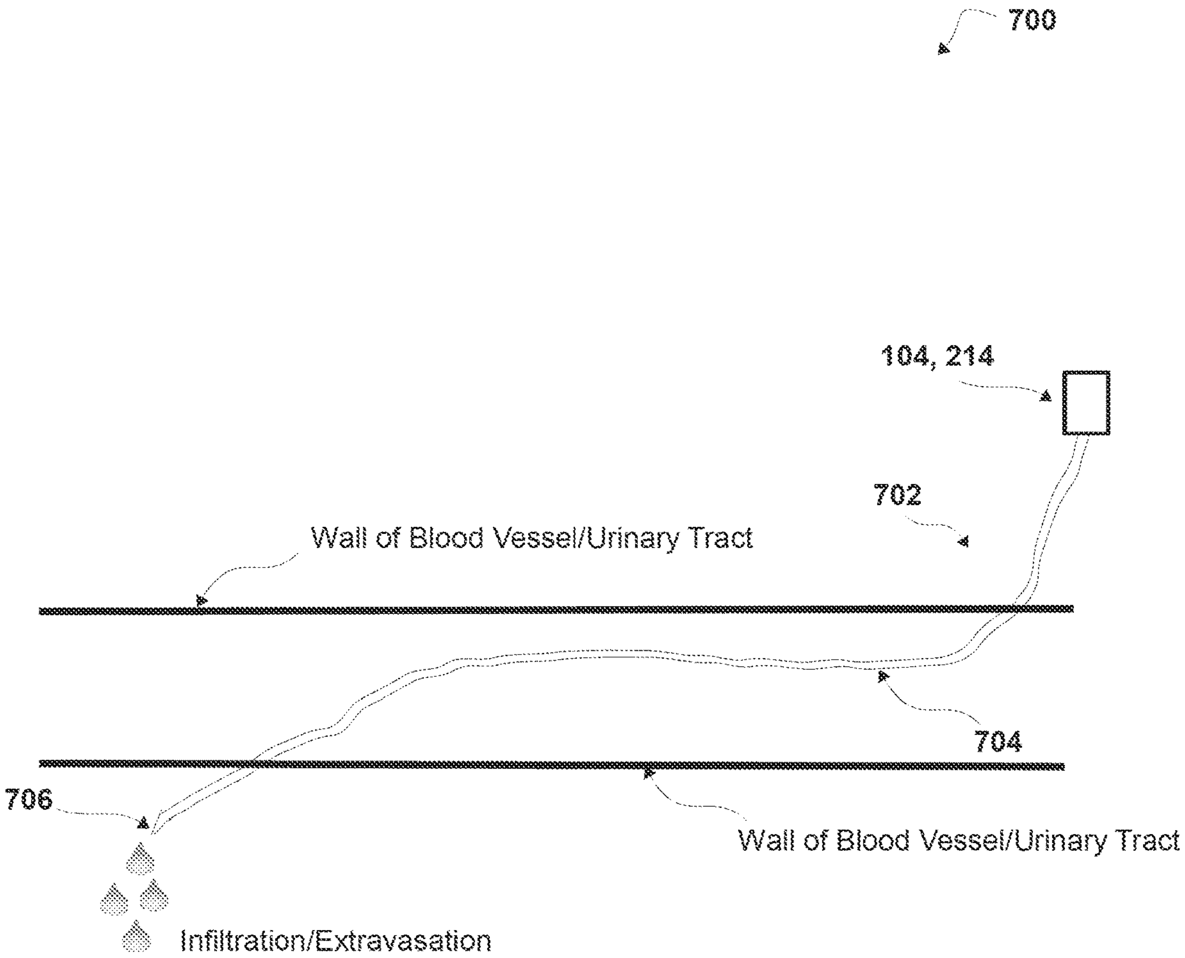
FIG. 7 is a diagram of non-limiting embodiments or aspects of an implementation of a smart device for detecting an extravasation and/or an infiltration of a medication in a catheter.

FIG. 7 is a diagram of non-limiting embodiments or aspects of an implementation 700 of a smart device for detecting an extravasation or an infiltration of a medication in a catheter. As shown in FIG. 7, smart device 104 may be connected to or integrated with a needleless connector 214 at a catheter hub of catheter 702 including a catheter lumen or line 704 and a needle tip 706 for delivering fluid to a patient at an opposite end of the catheter line 704 from smart device 104. Catheter 702 may be inserted in a blood vessel (e.g., a vein, an artery, etc.) of the patient. For example, the location of the tip 706 of the needle may be within the blood vessel of the patient, within a wall of the blood vessel or a wall of the urinary tract of the patient, or outside the blood vessel or the urinary tract and the wall of the blood vessel or the wall of the urinary tract of the patient. In some non-limiting embodiments or aspects, smart device 104 including catheter 702 may include a wired and/or a wireless transmitted configured to (e.g., via a wire, wirelessly, etc.) transmit the at least one signal (and/or a variation in the at least one signal over a period of time, a location of the tip of the needle with respect to a blood vessel or a urinary tract of the patient, etc.) to a remote computer system or processing device. However, in some non-limiting embodiments or aspects, catheter 702 may be configured for insertion in a blood vessel.

In some non-limiting embodiments or aspects, smart device 104 may include sensor 254 (e.g., as shown in FIG. 3) located outside a body of the patient (e.g., at needleless connector 214 at the hub of catheter 702 located outside of a body of the patient, and sensor 254 may be connected to the hub of catheter 702 outside the body of the patient, etc.). For example, sensor 254 may include at least one of a pressure sensor and an acoustic sensor (e.g., a piezoelectric transducer, etc.). As an example, sensor 254 including the pressure sensor and/or the acoustic sensor may be connected to catheter 802 at needleless connector 214 at the hub of catheter 792. For example, the hub of catheter 702 may include needleless connector 702 and/or smart device 104, and sensor 254 may be included in needleless connector 214. In such an example, sensor 254 may be configured to sense, detect, and/or measure a pressure signal, an acoustic signal, and/or temporal variations in the pressure signal and/or the acoustic signal with the catheter needle in the body of the patient. For example, the pressure signal and/or the acoustic signal sensed by sensor 254 may be transmitted through a fluid in the catheter and/or through material of the catheter (e.g., via needle tip 706, catheter lumen 704, the needleless connector 214, etc.) for sensing by sensor 254. As an example, the pressure signal and/or the acoustic signal sensed by sensor 254 may decrease or drop if needle tip 706 punctures a wall of a blood vessel or urinary tract of the patient. In such an example, a decrease and/or lack in the pressure signal (e.g., a decreased amplitude of a heart rate and/or a drop in blood pressure, etc.) may indicate a lack of a pressure signal associated with an absence of a blood pressure signal, thereby indicating an infiltration event.

In some non-limiting embodiments or aspects, smart device 104 may be programmed and/or configured to compare a relatively slower change or variation in a pressure signal over time (e.g., a relatively slower decrease in an amplitude of a heart rate and/or a drop in blood pressure, etc.) to a threshold level to determine an occlusion event rather than an infiltration event or an extravasation event. For example, an occlusion in a lumen may be at a relatively slow rate over time (e.g., as compared to an infiltration event, an extravasation even, a disconnection event, etc.), which slowly changes in the pressure signal sensed by sensor 254. As an example, smart device 104 may determine an occlusion event and provide an alert and/or automatically flush a lumen associated with the occlusion in response to detection of the occlusion event. In some non-limiting embodiments or aspects, smart device 104 may detect a disconnection event in response to detecting a pressure signal substantially equal to an atmospheric pressure by sensor 254, which indicates that a connection of catheter 702, e.g., needleless connector 214 is disconnected therefrom and provide an alert to a user to address the connection. In some non-limiting embodiments or aspects, smart device 104 may detect a kink in the catheter lumen 704 in response to detecting a pressure signal associated with an amplitude of a heart rate that suddenly or immediately drops to zero, as opposed to an occlusion in a lumen that may cause the amplitude of the heart rate to drop a relatively slower rate over time.

In some non-limiting embodiments or aspects, smart device 104 can provide, according to the pressure signal and/or the acoustic signal, a location of the tip of the needle with respect to a blood vessel or a urinary tract of the patient in real-time, thereby providing real-time feedback to a user as a catheter is being installed in a blood vessel or a urinary tract of patient to indicate whether the catheter is properly placed within the blood vessel or the urinary tract or if with one of a potential or existing infiltration of the fluid and a potential or existing extravasation of the fluid. For example, smart device 104 can determine, according to the pressure signal and/or the acoustic signal (e.g., based on a fluid pressure due to fluid entering a catheter path of smart device 104, etc.) a heart rate of a patient, a respiration rate of the patient, a blood pressure of the patient, a penetration force of a needle of the catheter, and/or the like. As an example, smart device 104 can provide, according to the pressure signal and/or the acoustic signal, an indication of entry of the tip of the needle into a blood vessel or a urinary tract of the patient in real-time.

Figure 8:
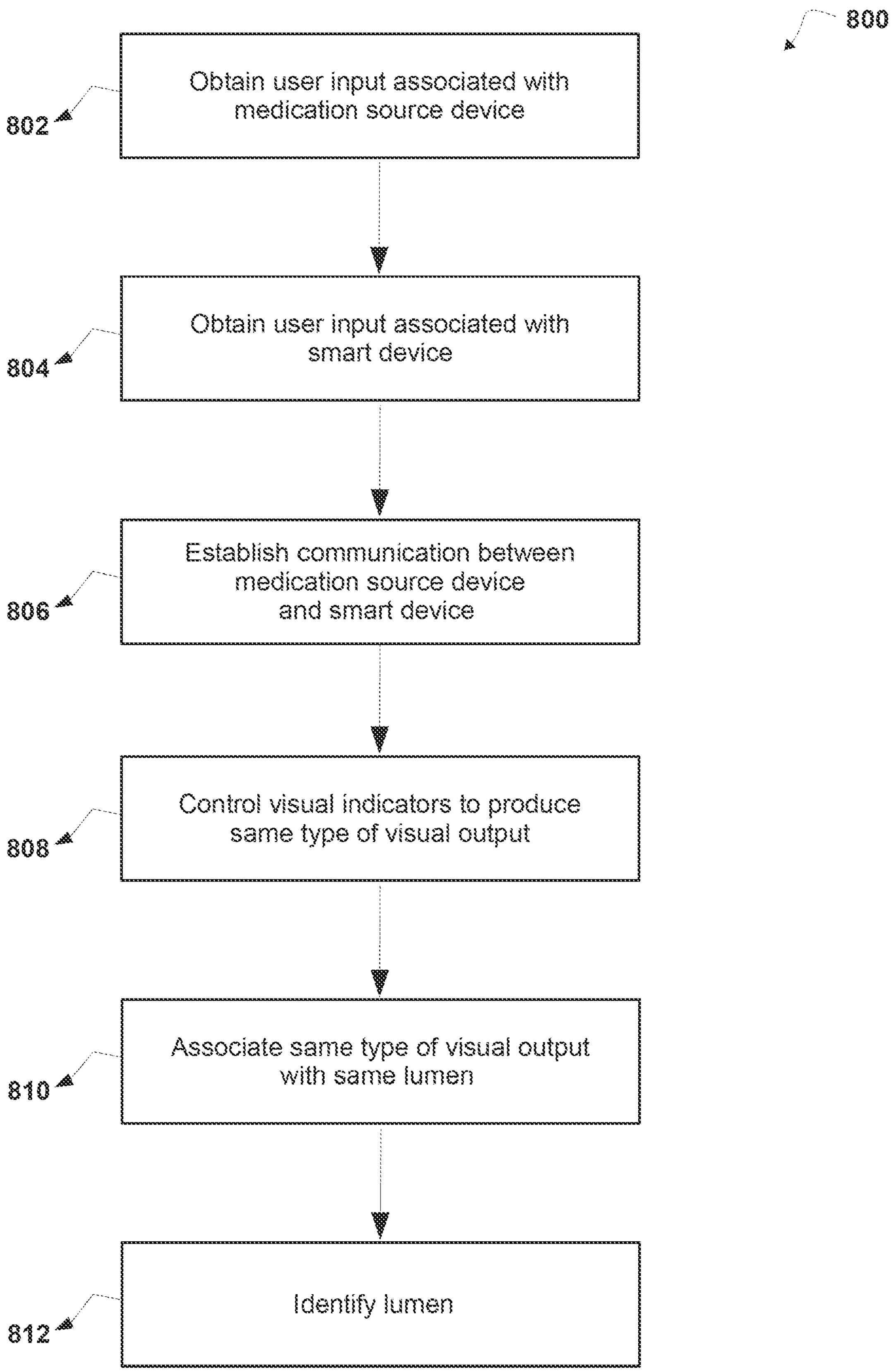
FIG. 8 is a flowchart of non-limiting embodiments or aspects of a process for identifying a lumen.

Referring now to FIG. 8, FIG. 8 is a flowchart of a non-limiting embodiment or aspect of a process 800 for identifying a lumen. In some non-limiting embodiments or aspects, one or more of the steps of process 800 are performed (e.g., completely, partially, etc.) by medication source system 102 (e.g., one or more devices of medication source system 102, etc.). In some non-limiting embodiments or aspects, one or more of the steps of process 800 are performed (e.g., completely, partially, etc.) by another device or a group of devices separate from or including medication source system 102, such as smart device 104 (e.g., one or more devices of a system of smart device 104, etc.), central computing system 108 (e.g., one or more devices of central computing system 108, etc.), and/or terminal/mobile computing system 110 (e.g., one or more devices of terminal/mobile computing system 110, etc.).

As shown in FIG. 8, at step 802, process 800 includes obtaining user input associated with a medication source device. For example, medication source system 102 may obtain user input associated with medication source device 206. As an example, medication source system 102 may obtain (e.g., receive, retrieve, determine, etc.) user input received via a user input component (e.g., via pairing input 208, etc.) of medication source device 206. In such an example, medication source system 102 may receive data associated with the user input from medication source device 206.

Referring also to FIG. 2A, in some non-limiting embodiments or aspects, a plurality of medication source devices 206*a*, 206*b*, . . . 206*n* of a medication source system 102 are connected to a plurality of lumens 212*a*, 212*b*, . . . 212*n*, and each medication source 206 device may include a visual indicator 210, communication circuitry (e.g., communication interface 314, etc.), and a paring input 208. In some non-limiting embodiments or aspects, medication source device 206 receives, via pairing input 208 of medication source device 206, user input. For example, visual indicator 210 may emit a predetermined light pattern (e.g., blink rapidly and/or emit a predetermined color to indicate that medication source device 206 is in a pairing mode, etc.) in response to a predetermined user input to pairing input 208 (e.g., in response to a user pressing and holding a button of pairing input 208, etc.) of medication source device 206.

As shown in FIG. 8, at step 804, process 800 includes obtaining user input associated with a smart device. For example, medication source system 102 may obtain user input associated with smart device 104. As an example, medication source system 102 may obtain (e.g., receive, retrieve, determine, etc.) user input received via a user input component (e.g., pairing input 256, etc.) of smart device 104. In such an example, medication source system 102 may receive data associated with the user input from smart device 104 that is received at a same time that medication source device 206 is in the pairing mode.

Referring also to FIGS. 2A and 2B, in some non-limiting embodiments or aspects, a plurality of smart devices 104*a*, 104*b*, . . . 104*n* may be connected (e.g., removably connected, etc.) or configured to be connected to the plurality of lumens 212*a*, 212*b*, . . . 212*n*, and each smart device 104 may include a visual indicator 252, communication circuitry (e.g., communication interface 314, etc.), and a paring input 256. In some non-limiting embodiments or aspects, smart device 104 receives, via pairing input 256 of smart device 104, user input. For example, smart device 104 may establish communication with medication source device 206 (e.g., pair and/or activate/initiate a pairing sequence for pairing smart device 104 with medication source device 206, etc.) in response to a predetermined user input to paring input 256 (e.g., in response to a user pressing and holding a button of pairing input 256, etc.) of smart device 104 at a same time that medication source device 206 is in the pairing mode.

As shown in FIG. 8, at step 806, process 800 includes establishing communication between a medication source device and a smart device. For example, medication source system 102 may establish communication between medication source device 206 and smart device 104. As an example, medication source system 102 may establish communication (e.g., an NFC communication connection, an RFID communication connection, a Bluetooth® communication connection, and/or the like) between medication source device 206 and smart device 104. In such an example, the communication circuitry of smart device 104 and the communication circuitry of medication source device 206 may establish the communication between (e.g., pair, etc.) smart device 104 and medication source device 206 based on the user input received by pairing input 208 of the medication source device 206 and the user input received by pairing input 256 of smart device 104. For example, medication source device 206 may establish a short range wireless communication connection (e.g., an NFC communication connection, an RFID communication connection, a Bluetooth® communication connection, etc.) with smart device 104. As an example, visual indicator 210 may be configured to emit a predetermined light pattern (e.g., to blink rapidly to indicate that medication source device 206 is in a pairing mode, etc.) in response to a predetermined user input to pairing input 208 (e.g., in response to a user pressing and holding a button of pairing input 208, etc.) of medication source device 206. In such an example, smart device 104 may be configured to establish communication with medication source device 206 (e.g., pair and/or activate a pairing sequence for pairing smart device 104 with medication source device 206, etc.) in response to a predetermined user input to paring input 256 (e.g., in response to a user pressing and holding a button of pairing input 256, etc.) of smart device 104 at a same time that medication source device 206 is in the pairing mode.

As shown in FIG. 8, at step 808, process 800 includes controlling visual indicators of a medication source device and a smart device to produce a same type of visual output. For example, medication source system 102 may control visual indicator 210 of medication source device 206 and visual indicator 252 of smart device 104 to produce a same type of visual output. As an example, medication source system 102 may control visual indicator 210 (e.g., a multi-color LED, etc.) of medication source device 206 and visual indicator 252 (e.g., a multi-color LED, etc.) of smart device 104 to produce a same type of visual output (e.g., a same color of light, etc.) based on the communication established between the medication source device and the smart device.

In some non-limiting embodiments or aspects, when smart device 104 is paired with medication source device 206, medication source device 206 may illuminate visual indicator 210 to a color that has not been previously used in medication source system 102 (e.g., that is not associated with another medication source device 206 and another smart device 104 that are paired in medication source system 102, that is different than each other color of light produced by each other smart device 104 of the plurality of smart devices 104*a,* 104*b,* . . . 104*n* and each other medication source device 206 of the plurality of medication source devices 206*a,* 206*b,* . . . 206*n* in medication source system 102, etc.), and smart device 104 may illuminate visual indicator 252 to the same color as visual indicator 210 (e.g., medication source system 102, medication source device 206, smart device 104, etc. may control visual indicator 252 5*o* illuminate to the same color as visual indicator 210). In some non-limiting embodiments or aspects, smart device 104 may illuminate visual indicator 252 to the same color as visual indicator 210 in response to smart device 104 being connected to a lumen and/or during a period of time at which smart device 104 is connected to the lumen. For example, smart device 104 may automatically stop illumination of visual indicator 252 to the same color as visual indicator 210 (e.g., turn off an LED, set the LED to a default color indicating a non-paired smart device 104, etc.) in response to smart device 104 being disconnected from the lumen. As an example, smart device 104 may include a switch connected to visual indicator 252 that is configured to be activated/deactivated in response to a clamp or other connection means being connected/disconnected to a lumen and/or a needleless connector 214 thereof.

In some non-limiting embodiments or aspects, medication source system 102 determines a color of the same color of light for visual indicator 252 of smart device 104 and visual indicator 210 of medication source device 206 to produce based on at least one of the user input received by pairing input 208 of medication source device 206 and the user input received by pairing input 256 of smart device 104. For example, after smart device 104 is paired with medication source device 206, a user may actuate pairing input 208 and/or pairing input 256 to cycle through colors of light available for the pairing to select a desired (and/or available or previously unused) color of light for the pairing.

As shown in FIG. 8, at step 810, process 800 includes associating a same type of visual output with a same lumen. For example, medication source system 102 may associate (e.g., automatically associate, etc.) a same type of visual output with a same lumen. As an example, medication source system 102 may associate (e.g., store in connection with, pair, link, illuminate with, etc.) the same type of visual output (e.g., a same color of light, etc.) with a same lumen (e.g., with a same lumen of a plurality of lumens 212*a,* 212*b,* . . . 212*n,* etc.). In such an example, medication source device 206 and smart device 104 may be connected to the same lumen. Accordingly, a user may more easily identify a lumen or line, a location of the lumen or line, a medication that has been or is being delivered via the lumen or line, which infusion pump or mediation source to which the lumen or line is connected, and/or the like.

In some non-limiting embodiments or aspects, medication source system 102 may obtain user input received by a user input component of another medication source device, obtain user input received by a user input component of another smart device, establish a communication between the another medication source device and the another smart device based on the user input received by the user input component of the another medication source device and the user input received by the user input component of the another smart device, control the visual indicator of the another smart device and the visual indicator of the another medication source device to produce another same type of visual output based on the communication established between the another medication source device and the another smart device, wherein the another same type of visual output is different than the same type of visual output, and/or associate the another same type of visual output with another same lumen of the plurality of lumens, wherein the another medication source device is connected to the another same lumen. For example, and referring again to FIG. 2A, medication source device 206*a* may be paired with smart device 104*n* and each of medication source device 206*a* and smart device 104*n* may output a first color of light (e.g., red light) associated with lumen 212*a,* medication source device 206*b* may be paired with smart device 104*a* and each of medication source device 206*b* and smart device 104*a* may output a second color of light (e.g., green light) associated with lumen 21*b,* medication source device 206*n* may be paired with smart device 104*b* and each of medication source device 206*n* and smart device 104*b* may output a third color of light (e.g., blue light) associated with lumen 212*n,* and/or the like.

As shown in FIG. 8, at step 812, process 800 includes identifying a lumen. For example, medication source system 102 may identify a lumen. As an example, medication source system 102 may identify the same lumen associated with the same type of visual output.

In some non-limiting embodiments or aspects, medication source system 102 identifies a lumen by automatically associating and/or providing medical data with the same type of visual output associated with the lumen and/or an identifier of the lumen. For example, medical data may include at least one of the following: patient data (e.g., an identifier of a particular patient, information and/or data associated with a patient, etc.); medication source data (e.g., an identifier of a particular medication source device 206, etc.); medication data (e.g., an identifier of a type of a medication, a scheduled delivery of a particular medication, a previous delivery of a particular medication, a lumen associated with a medication, etc.); lumen data (e.g., an identifier of a particular lumen, such as the identifier of the same lumen associated with the same type of visual output, etc.); sensor data (e.g., an identifier of a particular sensor 254, information, data, and/or a signal sensed, measured, and/or detected by one or more sensors 254 in one or more smart devices 104, etc.); compliance data (e.g., information or data associated with a scrubbing event in which a needleless connector 214 and/or a lumen is scrubbed with a disinfectant, information or data associated with a flushing event in which a needleless connector 214 and/or a lumen is flushed with a solution, information or data associated with a connection or capping event in which a needleless connector 214 or a lumen is connected to a medical device, etc.); location data (e.g., a location of a patient, a location a previous or scheduled fluid delivery procedure, a location a lumen, a location of a medication source device, etc.); time data (e.g., a time associated with a previous or scheduled fluid delivery procedure, a time of connection of a lumen to medication source device 206, a time of connection of smart device 104 to a lumen, a time of pairing of medication source device 206 and smart device 104, etc.); a location of a tip of a needle of a catheter of a lumen with respect to a blood vessel or urinary tract of the patient; or any combination thereof. As an example, medication source system 102 may obtain medical data from smart device 104, central computing system 108, terminal/mobile computing system 110, one or more databases connected thereto, and/or one or more sensors (e.g., a barcode sensor for scanning a patient identifier, a fluid flow sensor for sensing a flow a fluid, a medication type sensor for sensing a type of a medication, etc.) connected thereto. In such an example, medication source system 102 may identify lumens with information and/or data associated therewith, as well as provide a visual indication of which lumens of a plurality of lumens 212*a*, 212*b*, . . . 212*n* are connected to which medication source devices of a plurality of medication source devices 206*a*, 206*b*, . . . 206*n*, which can enable a user to more easily trace a lumen from a patient to a particular medication source device to which the lumen is connected; connections between lumens and medication source devices to be removed if the patient is moved (e.g., to a new room, to a new floor, to surgery, to the bathroom, etc.) with the same type of visual indicator on a lumen/medication source device pair used to more easily reattach the correct medication source device channel to the correct (e.g., the same as before) lumen; tracking compliance to best practice protocols, for example, by determining if hub scrubbing has occurred and if hub scrubbing occurred effectively (e.g., sufficient pressure, sufficient time scrubbing, etc.) and/or if a device has been flushed, maintained, and/or the like; providing reminders and prescriptive help for protocol adherence, and/or the like.

In some non-limiting embodiments or aspects, medication source system 102 identifies a lumen by determining and providing, based on the medical data, one or more alerts or reminders associated with the lumen and/or the same type of visual output associated with the lumen, such as a reminder to flush the lumen and/or a needleless connector 214 thereof, a reminder to remove or replace a lumen, BD MedMined™ infection prevention guidance (e.g., identification and reporting healthcare-associated infections (HAIs) and using customized alerts and reports to facilitate timely patient intervention, etc.), an alert to use a different lumen for delivery of a particular medication to reduce a chance of a chemical occlusion forming, an alert indicating whether to treat a lumen for thrombus occlusion or chemical occlusion, an alert that an occlusion is detected in a lumen, an alert that a location of a tip of a needle connected to the lumen is associated with one of a potential or existing infiltration of the fluid and a potential or existing extravasation of the fluid, and/or the like.

In some non-limiting embodiments or aspects, medication source system 102 identifies a lumen by controlling a medication source device 206 or another medical device (e.g., an electronic valve, etc.), based on the medical data, to inhibit or prevent delivery of a fluid (e.g., a particular medication, a type of medication, etc.) via the lumen.

Further details regarding non-limiting embodiments or aspects of step 812 of process 800 are provided below with regard to FIG. 9.

Figure 9:
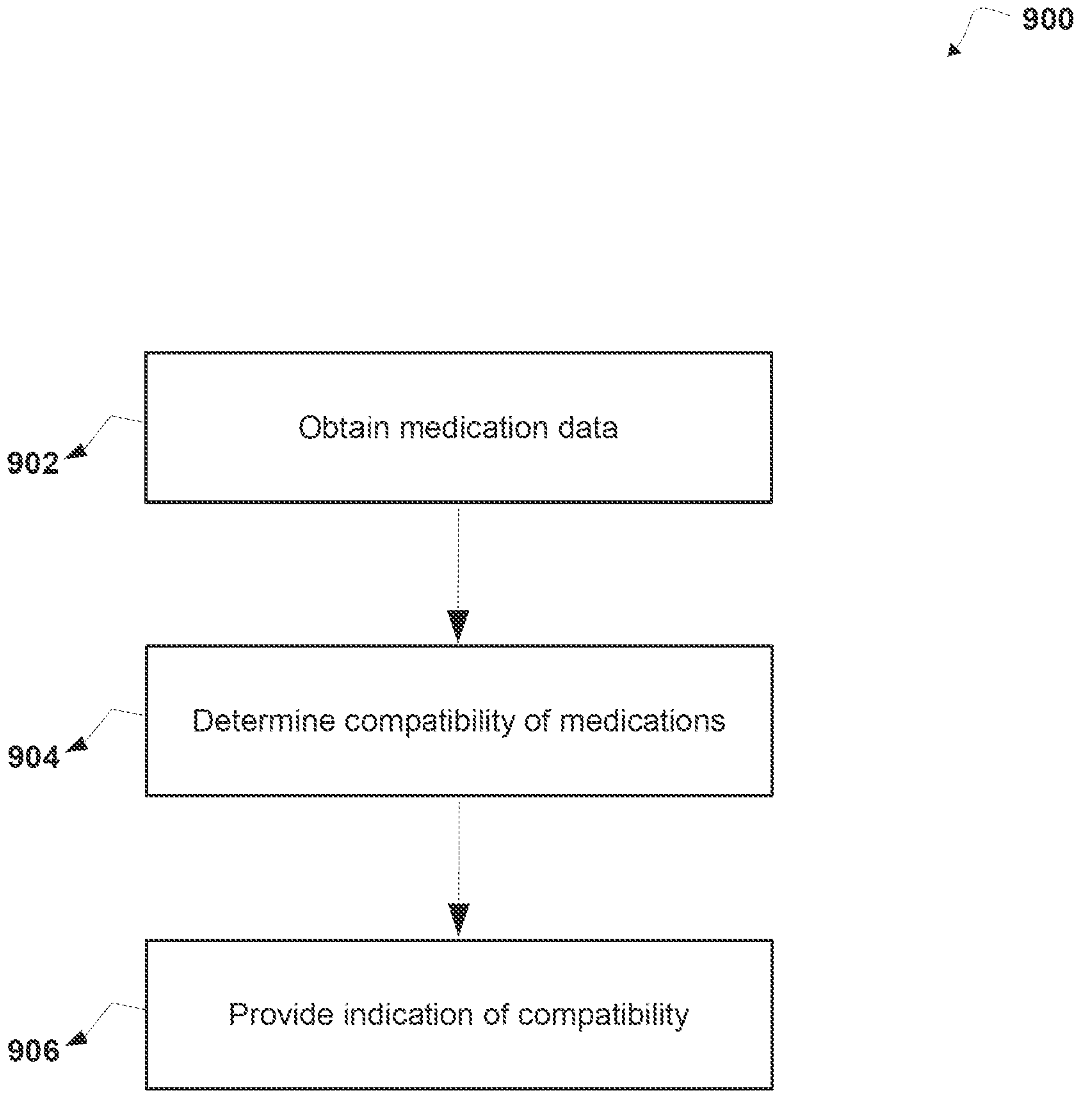
FIG. 9 is a flowchart of non-limiting embodiments or aspects of a process for identifying a lumen.

Referring now to FIG. 9, FIG. 9 is a flowchart of a non-limiting embodiment or aspect of a process 900 for identifying a lumen. In some non-limiting embodiments or aspects, one or more of the steps of process 900 are performed (e.g., completely, partially, etc.) by medication source system 102 (e.g., one or more devices of medication source system 102, etc.). In some non-limiting embodiments or aspects, one or more of the steps of process 900 are performed (e.g., completely, partially, etc.) by another device or a group of devices separate from or including medication source system 102, such as smart device 104 (e.g., one or more devices of a system of smart device 104, etc.), central computing system 108 (e.g., one or more devices of central computing system 108, etc.), and/or terminal/mobile computing system 110 (e.g., one or more devices of terminal/mobile computing system 110, etc.).

As shown in FIG. 9, at step 902, process 900 includes obtaining medication data. For example, medication source system 102 may obtain medication data. As an example, medication source system 102 may obtain medication data associated with a first type of medication delivered or scheduled to be delivered via the same lumen to a patient and a second type of medication delivered or scheduled to be delivered via the same lumen to the patient. In such an example, the first type of medication may be different than the second type of medication.

In some non-limiting embodiments or aspects, medication data is associated with at least one of the following: an identifier of a type of a medication, a scheduled delivery of the medication via a particular medication source device, and/or lumen, a previous delivery of the medication via a particular medication source device and/or lumen, an amount of the medication, an identifier of a patient to which the medication is scheduled to be delivered (or delivered), one or more identifiers of one or more different types of medication that are incompatible for delivery via a same lumen with the medication, and/or the like.

As shown in FIG. 9, at step 904, process 900 includes determining compatibility of medications. For example, medication source system 102 may determine compatibility of medications. As an example, medication source system 102 may determine, based on the medication data, a compatibility of the second type of medication for delivery via the same lumen as the first type of medication.

In some non-limiting embodiments or aspects, medication source system 102 may use an identifier of the first type of medication and/or an identifier of the second type of medication to access a look-up table that indicates whether the first type of medication and the second type of medication are compatible or incompatible (e.g., compatible or incompatible for delivery via a same lumen, etc.). In some non-limiting embodiments or aspects, the look-up table maybe be stored in and/or associated with the identifier of the first type of medication and/or the identifier of the second type of medication.

In some non-limiting embodiments or aspects, medication source device 102 may obtain medication data associated with a third type of medication delivered or scheduled to be delivered via another same lumen (e.g., different than the same lumen, etc.) to the patient, and determine, based on the medication data, a compatibility of the second type of medication for delivery via the another same lumen as the third type of medication, wherein the indication further indicates whether the second type of medication is compatible for delivery via the another same lumen associated with the another same type of visual output. For example, and referring again to FIGS. 2A and 2B, if medication source device 102 determines that the second type of medication is incompatible for delivery via a first lumen 212*a*, medication source device 102 may determine a compatibility of the second type of medication for delivery via an alternative lumen, such as a second lumen 212*b* based a third type of medication delivered or scheduled to be delivered via the second lumen 212*b* and, if the second type of medication is compatible for delivery via the same lumen as the third type of medication, provide the indication that the second type of medication is compatible for delivery via the second lumen 212*b*.

As shown in FIG. 9, at step 906, process 900 includes providing an indication of compatibility. For example, medication source system 102 may provide an indication of compatibility. As an example, medication source system 102 may provide an indication of whether the second type of medication is compatible for delivery via the same lumen associated with the same type of visual output. As another example, medication source system 102 may provide an indication of whether the third type of medication is compatible for delivery via the another same lumen associated with the another same time of visual output.

In some non-limiting embodiment or aspects, medication source system 102 may provide the indication of the compatibility by controlling medication source device 206 to inhibit or prevent delivery of the second medication via the same lumen associated with the same type of visual output. For example, the first type of medication may be delivered to the patient with the same lumen associated with the same type of visual output, and the second type of medication may be scheduled to be delivered via the same lumen to the patient. As an example, and referring again to FIGS. 2A and 2B, medication source system 102 may determine, based on the medical data including the medication data, that a first type of drug is delivered via lumen 212*a* to the patient and that a second type of drug that is scheduled for delivery or attempting to be delivered via the same lumen 212*a* is incompatible with the first type of drug (e.g., likely to cause an occlusion, likely to cause an adverse reaction in the patient, etc.). In such an example, medication source system 102 may control medication source device 206*a* to inhibit or prevent delivery of the second medication via the same lumen 212*a* (e.g., by stopping a pump, closing a valve, etc.) and/or providing a prompt to the user to use another lumen (e.g., 212*b*, . . . 212*n*, etc.) associated with a different type of visual output than the same type of visual output to deliver the second type of medication to the patient.

In some non-limiting embodiments or aspects, the first type of medication and the second type of medication may be delivered to the patient via the same lumen associated with the same type of visual output, and medication source system 102 may provide a prompt to the user to treat the same lumen associated with the same type of visual output for one of a thrombus occlusion and a chemical occlusion. For example, when an occlusion occurs, which may be detected by medication source system 102 as described herein, a user (e.g., a nurse, etc.) may need to determine if the occlusion is thrombotic or chemical due to drug interactions, and medication source system 102 can determine which medications were delivered via which lumens to inform the user of the lumen history and/or provide an indication of a potential cause of the occlusion, which enables a correct decision of whether the lumen should be treated for thrombus or chemical occlusion. In some non-limiting embodiments or aspects, medication source system 102 may control medication source device 206 to automatically perform a flushing operation to deliver a flushing fluid to a lumen connected to the medication source device 206 in response to a determination that an occlusion of the lumen is a chemical occlusion.

Figure 10:
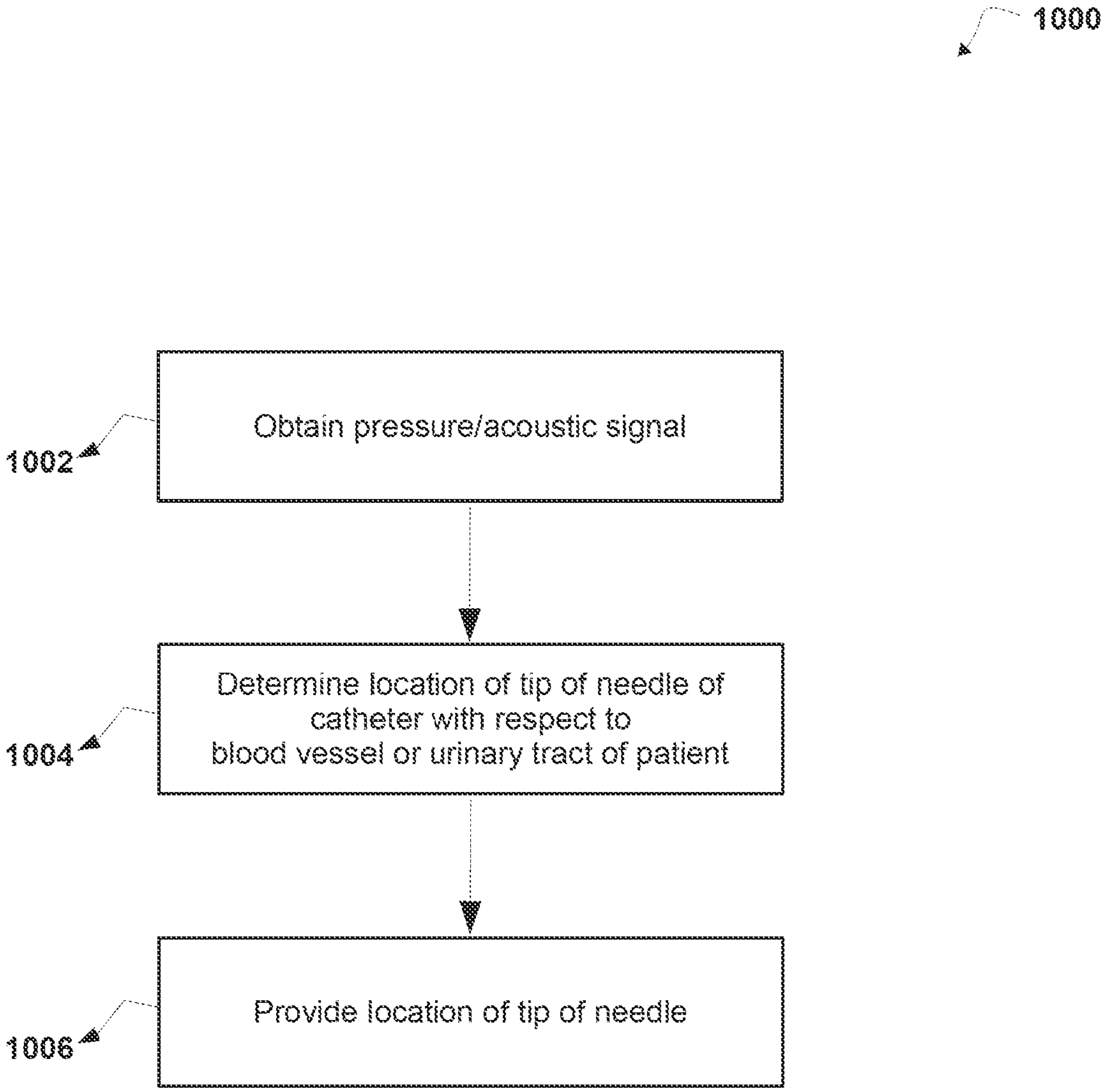
FIG. 10 is a flowchart of non-limiting embodiments or aspects of a process for locating a needle tip.

Referring now to FIG. 10, FIG. 10 is a flowchart of a non-limiting embodiment or aspect of a process 1000 for locating a needle tip. In some non-limiting embodiments or aspects, one or more of the steps of process 1000 are performed (e.g., completely, partially, etc.) by smart device 104 (e.g., one or more devices of a system of smart device 104, etc.). In some non-limiting embodiments or aspects, one or more of the steps of process 1000 are performed (e.g., completely, partially, etc.) by another device or a group of devices separate from or including smart device 104, such as medication source system 102 (e.g., one or more devices of medication source system 102, etc.), central computing system 108 (e.g., one or more devices of central computing system 108, etc.), and/or terminal/mobile computing system 110 (e.g., one or more devices of terminal/mobile computing system 110, etc.).

As shown in FIG. 10, at step 1002, process 1000 includes obtaining a signal including at least one of a pressure signal and an acoustic signal. For example, smart device 104 may obtain a signal including at least one of a pressure signal and an acoustic signal from at least one sensor connected to a catheter. As an example, smart device 104 may obtain at least one signal including at least one of a pressure signal and an acoustic signal from sensor 254 (e.g., from a pressure sensor, from an acoustic sensor, etc.) connected to catheter 702. In some non-limiting embodiments or aspects, and referring also to FIG. 7, catheter 702 includes a needle having tip 706 for delivering a fluid to a patient.

In some non-limiting embodiments or aspects, sensor 254 measures at least one signal including at least one of a pressure signal and an acoustic signal. For example, sensor 254 may measure the at least one signal including at least one of a pressure signal and an acoustic signal, and smart device 104 (and/or medication source system 102, central computing system 108, and/or terminal/mobile computing system 110) may obtain the at least one signal including at least one of a pressure signal and an acoustic signal from sensor 254. For example, smart device 104 may include communication circuitry (e.g., communication interface 314, etc.) that wirelessly transmits the at least one signal to a remote computing system. As an example, smart device 104 may process the pressure signal and/or the acoustic signal on a microprocessor within a housing of smart device 104 including sensor 254 and the microprocessor, and/or smart device 104 may wirelessly transmit (and/or transmit via wired connection) the pressure signal and/or the acoustic signal to a remote computer that perform digital signal processing on the pressure signal and/or the acoustic signal, to identify and classify events of interest (e.g., infiltration, extravasation, catheter occlusion, etc.).

As shown in FIG. 10, at step 1004, process 1000 includes determining a location of a tip of a needle of a catheter with respect to a blood vessel or a urinary tract of a patient. For example, smart device 104 may determine a location of a tip of a needle with respect to a blood vessel or a urinary tract of a patient. As an example, smart device 104 may determine, based on a variation in the at least one signal over a period of time, a location of tip 706 of the needle with respect to a blood vessel or a urinary tract of the patient.

In some non-limiting embodiments or aspects, the location of tip 706 of the needle is determined as one of: within the blood vessel or the urinary tract; within a wall of the blood vessel or a wall of the urinary tract; and outside the blood vessel or the urinary tract and the wall of the blood vessel or the wall of the urinary tract. In some non-limiting embodiments or aspects, smart device 104 and/or one or more components thereof may be connected to or included in (e.g., be integrated with, etc.) a needleless connector 214 at a catheter hub of catheter 702 located outside the body of the patient. For example, sensor 254 of smart device 104 (e.g., a pressure sensor, an acoustic sensor, etc.) may measure at least one signal including at least one of a pressure signal and an acoustic signal, wherein the catheter includes a needle having a tip for delivering a fluid to a patient.

In some non-limiting embodiments or aspects, smart device 104 determines that the location of tip 706 of the needle is associated with one of a potential or existing infiltration of the fluid and a potential or existing extravasation of the fluid. For example, sensor 254 (e.g., one or more pressure sensors, one or more acoustic sensors, etc.) may detect temporal variations in a pressure signal and/or an acoustic signal resulting from tip 706 of the needle of the catheter 702 being properly inserted in a blood vessel or urinary tract, being located in a wall of the blood vessel or urinary tract, being located outside the blood vessel or urinary tract, and/or the like. As an example, smart device 104 may compare the variation in the at least one signal over the period of time to a threshold variation associated with a heartbeat of the patient. For example, the variations in a pressure signal and/or an acoustic signal may be associated with variations in pressure and/or acoustics in a blood vessel or urinary tract as a result of a heartbeat of the patient. As an example, smart device 104 may compare the variations in the detected pressure signal and/or the detected acoustic signal to variations in a pressure signal and/or an acoustic associated with a heartbeat of the patient to determine if tip 706 of the needle of catheter 702 is properly located within the blood vessel (e.g., artery, vein, etc.) of the patient. In such an example, if tip 706 of the needle of catheter 702 overshoots the vessel or urinary tract (e.g., punctures a wall of the blood vessel or urinary tract, is not properly within the blood vessel or urinary tract, etc.) the pressure and/or acoustic signature of the at least one signal measured by sensor 254 changes. In some non-limiting embodiments or aspects, infiltration or extravasation of medication into tissues surrounding the blood vessel or urinary tract (rather than into the blood vessel or urinary tract) may result in distinctive pressure or acoustic signals being detected by sensor 254 depending upon the impact of the infiltration or extravasation on surrounding tissues (e.g., if the extravasating medication is a strong vesicant agent such impacts may be severe, etc.).

In some non-limiting embodiments or aspects, smart device 104 determines, based on the variation in the at least one signal over the period of time, at least one of an occlusion of the catheter and a disconnection of the catheter from a needleless connector. For example, smart device 104 may compare the variation in the at least one signal over the period of time to a threshold period of time associated with formation of an occlusion in a catheter. As an example, smart device 104 may compare a relatively slower change or variation in a pressure signal over time (e.g., a relatively slower decrease in an amplitude of a heart rate and/or a drop in blood pressure as compared to an infiltration or extravasation, etc.) to a threshold level to determine an occlusion event rather than an infiltration event or an extravasation event. For example, an occlusion in a lumen may develop at a relatively slow rate over time (e.g., as compared to an infiltration event, an extravasation even, a disconnection event, etc.), which slowly changes the pressure signal sensed may sensor 254. As an example, smart device 104 may determine an occlusion event and provide an alert and/or automatically flush a lumen associated with the occlusion in response to detection of the occlusion event. In some non-limiting embodiments, smart device 104 may detect a disconnection event in response to detecting a pressure signal substantially equal to an atmospheric pressure by sensor 254, which indicates that a connection of catheter 702, e.g., needleless connector 214 is disconnected therefrom and provide an alert to a user to address the connection.

As shown in FIG. 10, at step 1006, process 1000 includes providing a location of a tip of a needle. For example, smart device 104 may provide a location of a tip of a needle. As an example, smart device 104 may provide the location of tip 706 of the needle with respect to the blood vessel or urinary tract of the patient.

In some non-limiting embodiments or aspects, smart device 104 controls a warning device to issue a warning associated with the one of the potential or existing infiltration of the fluid and the potential or existing extravasation of the fluid. For example, smart device 104 controls visual indicator 252 of smart device 104 to output a color and/or a pattern of light associated with the one of the potential or existing infiltration of the fluid and the potential or existing extravasation of the fluid. As an example, in response to determining an event as infiltration, extravasation, or catheter occlusion, smart device 104 may flash a warning light to a user (e.g., a clinician, a caregiver, a family member, another patient in a homecare or assisted living environment, etc.) and/or transmit a signal to a remote computing system (e.g., medication source system 102, central computing system 108, terminal/mobile computing system 110, etc.) to control (e.g., trigger) output of an audio and/or visual alarm at the remote computing system to alert appropriate individuals of the determined event.

In some non-limiting embodiments or aspects, smart device 104 controls medication source device 206 or a valve (e.g., a valve controlling fluid delivery to/from catheter 702, etc.) to stop (e.g., inhibit, prevent, etc.) delivery of the fluid to the catheter and/or from the catheter. As an example, in response to determining an event as infiltration, extravasation, catheter occlusion, or catheter disconnection smart device 104 may send a signal to an infusion device to immediately stop medication infusion or send a signal to a valve or mechanical clamp to block further medication from infusing into the catheter and/or the patient.

In some non-limiting embodiments or aspects, smart device 104 and/or needleless catheter may include communication circuitry (e.g., communication interface 314, etc.) that wirelessly transmits the at least one signal to a remote computing system. As an example, smart device 104 and/or needleless connector 214 may process the pressure signal and/or the acoustic signal on a microprocessor within housing 250 of smart device 104 and/or within housing 402 of needleless connector 214 including sensor 254 and the microprocessor, and/or smart device 104 and/or needleless connector 214 may wirelessly transmit (and/or transmit via a wired connection) the pressure signal and/or the acoustic signal to a remote computer that performs digital signal processing on the pressure signal and/or the acoustic signal, to identify and classify events of interest (e.g., infiltration, extravasation, catheter occlusion, catheter disconnection, etc.).

In some non-limiting embodiments or aspects, smart device 104 may provide real-time feedback during catheter insertion (e.g., via visual indicator 252, output component 312, medication source system 102, etc.) such that a clinician or other person may be alerted as to whether catheter 702 is being properly inserted and/or as to whether tip 706 of the needle of catheter 702 has pierced or is in the process of piercing a blood vessel or a urinary tract and/or has been accidentally disconnected or occluded.

Figure 11:
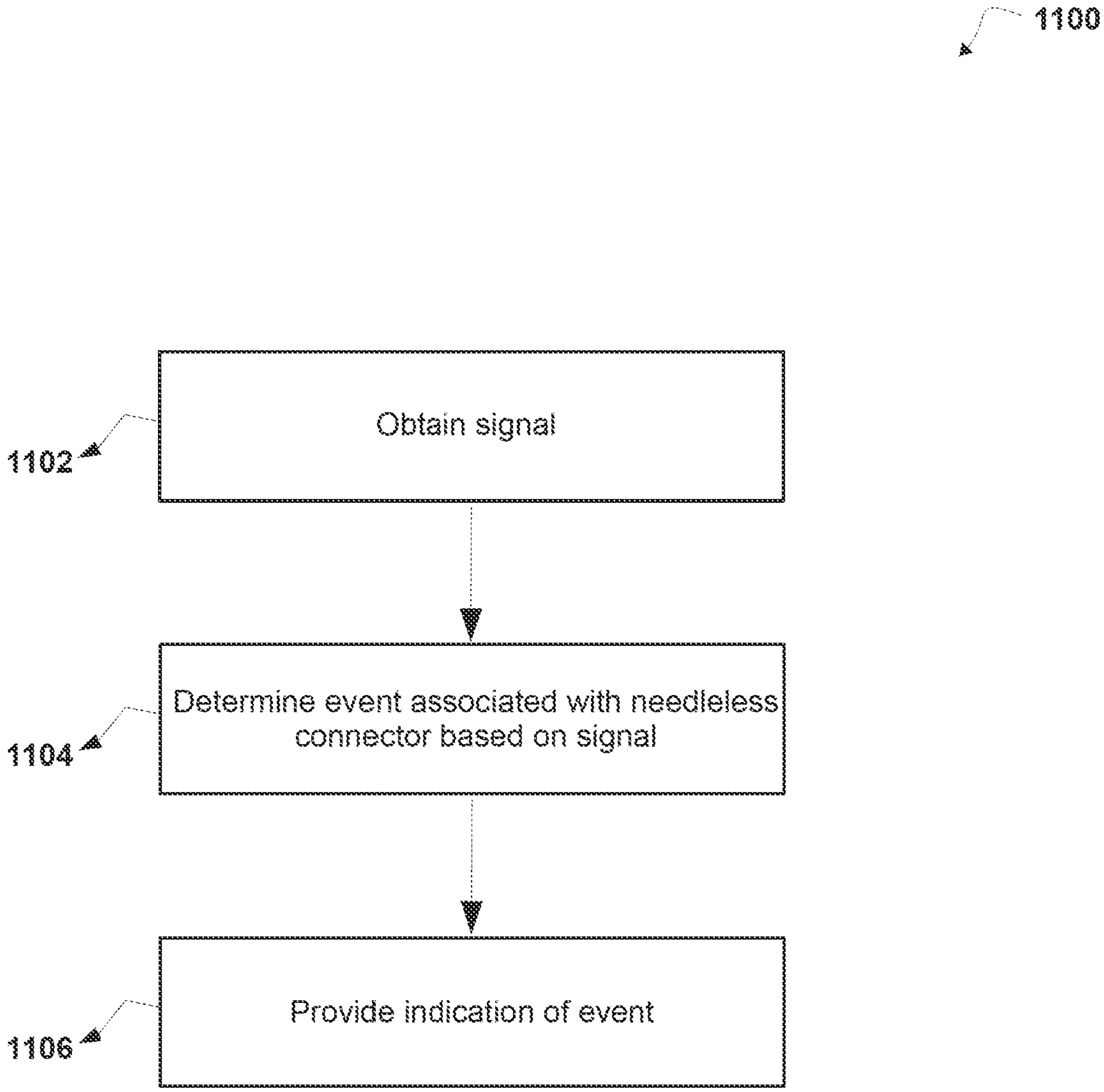
FIG. 11 is a flowchart of non-limiting embodiments or aspects of a process for event monitoring.

Referring now to FIG. 11, FIG. 11 is a flowchart of a non-limiting embodiment or aspect of a process 1100 for compliance event monitoring. In some non-limiting embodiments or aspects, one or more of the steps of process 1100 are performed (e.g., completely, partially, etc.) by smart device 104 (e.g., one or more devices of a system of smart device 104, etc.). In some non-limiting embodiments or aspects, one or more of the steps of process 1100 are performed (e.g., completely, partially, etc.) by another device or a group of devices separate from or including smart device, such as medication source system 102 (e.g., one or more devices of medication source system 102, etc.), central computing system 108 (e.g., one or more devices of central computing system 108, etc.), and/or terminal/mobile computing system 110 (e.g., one or more devices of terminal/mobile computing system 110, etc.).

As shown in FIG. 11, at step 1102, process 1100 includes obtaining a signal. For example, smart device 104 may obtain a signal. As an example, smart device 104 may obtain a signal (e.g., a force signal, a signal other than a force signal, such as an optical signal, a flow signal, an acoustic signal, a sound signature, a signal associated with a septum movement, a pressure signal, and/or the like, etc.) measured by a sensor 254 (e.g., a force sensor, an optical sensor, a flow sensor, an acoustic sensor, a pressure sensor, etc.) connected to a needleless connector 214 including a fluid flow path. In such an example, sensor 254 may measure, with a sensor connected to a needleless connector including a fluid flow path, a signal, and smart device 104 (and/or medication source system 101, central computing system 108, terminal/mobile computing system 100, etc.) may obtain the signal from sensor 254.

In some non-limiting embodiments or aspects, a signal obtained by smart device 104 may include a measurement of a value at an instantaneous, static, or single point in time (e.g., a force, a pressure, a sound, a vibration, a reflectance, and/or the like, at a single point in time, etc.). In some non-limiting embodiments or aspects, a signal obtained by smart device 104 may include a dynamic or time-varying signal (e.g., a measurement of a value over a period of time, etc.). For example, a time varying force, pressure, stress, strain, and/or the like may include low frequency signal, such as a signal that changes in sub-audible frequencies (e.g., below 20 Hz, etc.), and/or the like, and/or may include a signal in the acoustic range that travels as sound waves propagating through solids, liquids, and/or air. As described in more detail herein with respect to sensor 254, a time-varying signal may be measured with a force sensor, a seismograph, a pressure sensor, an optical sensor, a microphone, an acoustic sensor for air waves in the audible range, a hydrophone, an acoustic sensor for liquid waves, a pickup or a transducer that captures or senses mechanical vibrations, or any combination thereof.

As shown in FIG. 11, at step 1104, process 1100 includes determining an event associated with a needleless connector based on a signal. For example, smart device 104 may determine an event associated with a needleless connector 214 based on a signal. As an example, smart device 104 may determine, based on the signal (e.g., a force signal, a signal other than a force signal, such as an optical signal, a flow signal, an acoustic signal, a sound signature, a signal associated with a septum movement, a pressure signal, and/or the like, etc.), at least one of: a scrubbing event in which the needleless connector is scrubbed with a disinfectant, a flushing event in which the needleless connector is flushed with a solution, a connection event in which the needleless connector is connected to a medical device, a disconnection event in which the needleless connector is disconnected from the medical device, or any combination thereof.

In some non-limiting embodiments or aspects, sensor 254 may include force sensor 502. In some non-limiting embodiments or aspects, force sensor 502 includes at least one of: a piezoelectric element, a force sensitive resistive (FSR) sensor, a strain gauge, or any combination thereof. In some non-limiting embodiments or aspects, force sensor 502 is positioned between an outer surface of inner wall 510 (e.g., an inner harder plastic wall) of needleless connector 214 defining the fluid flow path of needleless connector 214 and an inner surface of an outer wall 512 (e.g., a softer, a more flexible, a more pliable, a rubber, etc. wall) of needleless connector 214 surrounding the inner wall 510 of needleless connector 214. In some non-limiting embodiments or aspects, an area between an outer surface of inner wall 510 (e.g., an inner harder plastic wall) of needleless connector 214 defining the fluid flow path of needleless connector 214 and an inner surface of an outer wall 512 (e.g., a softer, a more flexible, more, a more pliable, a rubber, etc. wall) of needleless connector 214 surrounding the inner wall 510 of needleless connector 214, which may be held by a user during cleaning and/or connection to another medical device, may be filled with a rubber or other pliable type material 514 including force sensors 502 as force sensing films within the material 514 between the inner wall 510 and the outer wall 512. In some non-limiting embodiments or aspects, force sensors 502 may be located between inner wall 510 and outer wall 512 below threading on and/or proximal to inlet 404 of needleless connector 214.

In some non-limiting embodiments or aspects, force sensor 502 includes a plurality of force sensors 502 positioned around the fluid flow path of needleless connector 214 between the outer surface of inner wall 510 of needleless connector 214 defining the fluid flow path of needleless connector 214 and the inner surface of outer wall 512 of needleless connector 214 surrounding inner wall 510 of needleless connector 214. For example, inlet 404 of needleless connector 214 may include septum 408 including a surface facing in a first direction, and force sensor 502 may be configured to detect a force in a second direction perpendicular to the surface of the septum facing in the first direction. As an example, the flushing event, which may include a pulsatile flushing event, may be determined based on the force signal indicating periodic forces in the second direction perpendicular to the surface of the septum facing in the first direction.

In some non-limiting embodiments or aspects, sensor 254 includes a pressure sensor, and the pressure sensor is one of: in direct contact with a fluid in the fluid flow path of the needleless connector; located within an inner wall of the needleless connector defining the fluid flow path of the needleless connector, and located within a wall of a lumen connected to the needleless connector. For example, smart device 104 may determine or detect pulsatile flush, a flush, and or a med-administration by the pressure sensor in contact with the fluid path in the needleless connector 214 and/or a lumen thereof.

In some non-limiting embodiments or aspects, the pressure sensor may be configured to sense a pressure transmitted through at least one of a fluid in a catheter and a material of the catheter. For example, and referring again to FIG. 7, needleless connector 214 may be connected to a catheter hub of a catheter 702 including a catheter lumen 704 and a needle tip 706 for delivering fluid to a patient at an opposite end of the catheter lumen 704 from the catheter hub. As an example, the pressure sensor may be connected to the needleless connector 214 to sense the pressure. In such an example, smart device 104 may receive, from the pressure sensor, a signal associated with the sensed pressure and determine, based on the signal, an event associated with the catheter 702.

In some non-limiting embodiments or aspects, the event associated with the catheter 702 includes a time at which the needle tip 706 of the catheter 702 enters a blood vessel of the patient. For example, smart device 104 may determine the time at which the needle tip 706 of the catheter 702 enters the blood vessel based on at least one: of a heart rate, a respiration rate, a blood pressure, a penetration force of the needle tip 706, or any combination thereof, determined from the signal associated with the sensed pressure.

In some non-limiting embodiments or aspects, the event associated with the catheter 702 includes a clamping sequence, and smart device 104 may determine the clamping sequence based on one or more changes over time in the signal associated with the sensed pressure. In such an example, smart device 104 may determine, based on the determined clamping sequence and a type of the needleless connector 214 (e.g., a neutral displacement connector, a positive displacement connector, a negative displacement connector, etc.), whether the determined clamping sequence satisfies a clamping protocol associated with the type of the needleless connector 214. For example, different types of needleless connector 214 (e.g., neutral displacement connectors, positive displacement connectors, negative displacement connectors, etc.) may be associated with different clamping protocols recommended to be performed during connection events and/or disconnection events to reduce or prevent backflow into catheter 702. As an example, not following a claiming protocol associated with the type of needleless connector 214 connected to the catheter 702 may result in an occlusion in the catheter 702 or an infection of the patient due to a backflow into the catheter 702. Accordingly, smart device 104 may reduce or prevent such occlusions and/or infections by monitoring whether a user performs the recommended clamping protocol associated with the particular type of needleless connector 214 connected to catheter 702.

In some non-limiting embodiments or aspects, the event associated with the cathether 702 includes an occlusion of the catheter lumen 704, and smart device 104 may determine the occlusion of the catheter lumen 704 based on a rate of change in the sensed pressure included in the signal from the pressure sensor. For example, smart device 104 may be programmed and/or configured to compare a relatively slower change or variation in a pressure signal over time (e.g., a relatively slower decrease in an amplitude of a heart rate and/or a drop in blood pressure, etc.) to a threshold level to determine an occlusion event rather than an infiltration event or an extravasation event. For example, an occlusion in a lumen may be at a relatively slow rate over time (e.g., as compared to an infiltration event, an extravasation even, a disconnection event, etc.), which slowly changes in the pressure signal sensed by sensor 254. As an example, smart device 104 may determine an occlusion event and provide an alert and/or automatically flush a lumen associated with the occlusion in response to detection of the occlusion event. In such an example, smart device 104 may detect a kink in the catheter lumen 704 in response to detecting a pressure signal associated with an amplitude of a heart rate that suddenly or immediately drops to zero, as opposed to an occlusion in a lumen that may cause the amplitude of the heart rate to drop at relatively slower rate over time.

In some non-limiting embodiments or aspects, sensor 254 includes an optical sensor configured to detect a movement of a septum 408 of needleless connector 214. For example, the optical sensor may be connected to the needleless connector including septum 408 to detect a movement of the septum 408. As an example, smart device 104 may receive, from the optical sensor, a signal associated with the movement of the septum and determine, based on the signal, an event associated with the needleless connector 214. For example, the event associated with the needleless connector may include at least one of: a connection event in which the needleless connector 214 is connected to a medical device (e.g., a syringe, a male luer connection, etc.) causing the movement (e.g., a depression, etc.) of septum 408, a disconnection event in which the needleless connector is disconnected from the medical device cause the movement (e.g., release, etc.) of septum 408, or any combination thereof. As an example, septum 408 may include one or more markings, and the optical sensor may be configured to detect a movement of the one or more markings to detect the movement of the septum 408.

In some non-limiting embodiments or aspects, sensor 254 includes an optical sensor configured to detect at least one of a color signature and a reflectance of a medical device connected to and/or being connected to needleless connector 214, and smart device 104 may determine a type of the medical device based on the at least one of the color signature and the reflectance of the medical device. For example, a color signature and/or the reflectance of the medical device may be indicative of a syringe, an IV bag, an infusion pump, and/or a particular type thereof.

In some non-limiting embodiments or aspects, sensor 254 includes an acoustic sensor. For example, the acoustic sensor may be connected to needleless connector 214 and configured to measure one or more sounds, vibrations, and/or the like (e.g., a sound signature, etc.). As an example, smart device 104 may receive, from the acoustic sensor, a signal including a sound signature, and determine, based on the signal, an event associated with needleless connector 214.

In some non-limiting embodiments or aspects, the event associated with the needleless connector 214 includes (i) a connection event in which the needleless connector 214 is connected to a medical device (e.g., a syringe, a cap, etc.) and/or (ii) an operation of a medical device connected to the needleless connector 214. In such an example, smart device 104 may determine, based on the sound signature (e.g., a sound signature generated from connecting the needleless connector 214 to the medical device, a sound signature generated from operation of the medical device connected to needleless connector 214, one or more ticking sounds, etc.), a type of the medical device connected to the needleless connector 214 from a plurality of types of medical devices and/or a state of the medical device connected to the needleless connector 214. For example, the plurality of types of medical devices may include two or more of the following: a cap, a syringe, a tubing, a medical device connector, or any combination thereof. In some non-limiting embodiments or aspects, smart device 104 may determine, based on the sound signature, a subtype of the determined type of the medical device connected to the needleless connector from a plurality of subtypes of that type of medical device, such as a subtype of a syringe (e.g., a syringe size, a flush syringe, a medication administration syringe, etc.), a subtype of a cap (e.g., a disinfectant cap, etc.), and/or the like. In some non-limiting embodiments or aspects, a state of a medical device includes an unused state or a used state.

Figure 12:
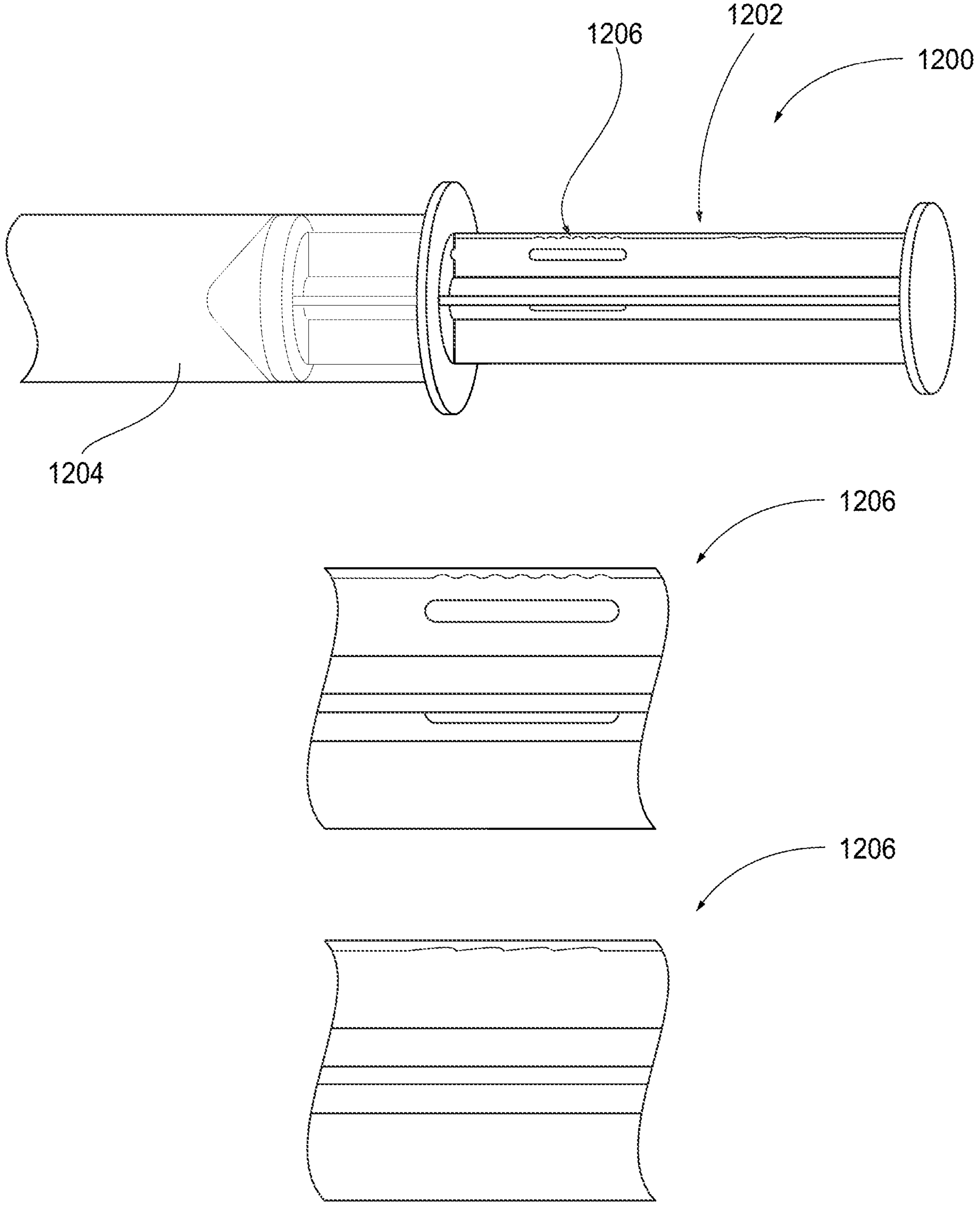
FIG. 12 is a side view of non-limiting embodiments or aspects of an implementation of a syringe.

In some non-limiting embodiments or aspects, and referring also to FIG. 12, the medical device includes a syringe 1200. For example, operation of the syringe 1200 may include depression of a plunger 1202 of the syringe 1200 into a barrel 1204 of the syringe 1200, and depression of the plunger 1202 of the syringe 1200 into the barrel 1204 of the syringe 1200 may generate the sound signature (e.g., one or more ticking sounds, etc.). As an example, the plunger 1202 of the syringe 1200 may include one or more extrusions 1206 (e.g., corresponding to the one or more ticking sounds, etc.) that generate the sound signature in combination with the barrel 1204 when the plunger 1202 of the syringe 1200 is depressed into the barrel 1204 of the syringe 1200. In such an example, smart device 104 may differentiate a type and/or state of the syringe 1200 based on the sound signature sensed by the acoustic sensor. For example, the extrusions 1206 may be located or configured to provide an indication of whether a syringe is unused or new (e.g., with plunger 1202 fully extended, which generates a first sound signature in response to depression of plunger 1202 into barrel 1204, etc.) or being re-used (e.g., with plunger 1202 extended half-way, which generates a second sound signature different than the first sound signature (or nor sound signature) in response to further depression of plunger 1202 into barrel 1204, etc.). In some non-limiting embodiments or aspects, a state of the medical device includes a volume of fluid expelled from the syringe when the plunger 1202 of the syringe 1200 is depressed into the barrel 1204 of the syringe 1200. For example, the extrusions 1206 may be located or configured to provide a sound signature associated with an indication of a volume applied by syringe 1200 in response to depression of plunger 1202 within barrel 1204.

Figure 13A:
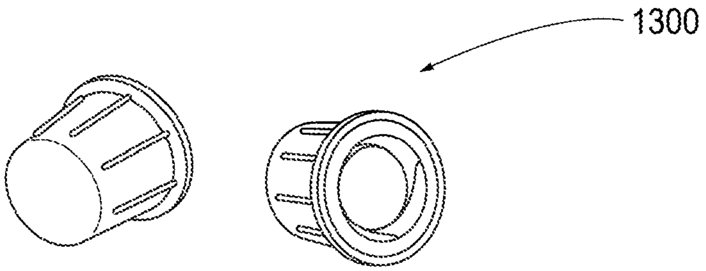
FIGS. 13A-13C are perspective and side views of non-limiting embodiments or aspects of an implementation of a disinfectant cap.
Figure 13B:
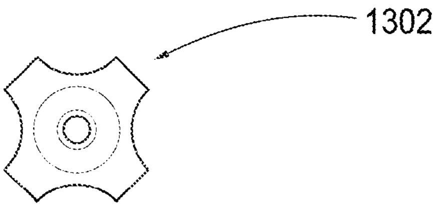
Figure 13C:
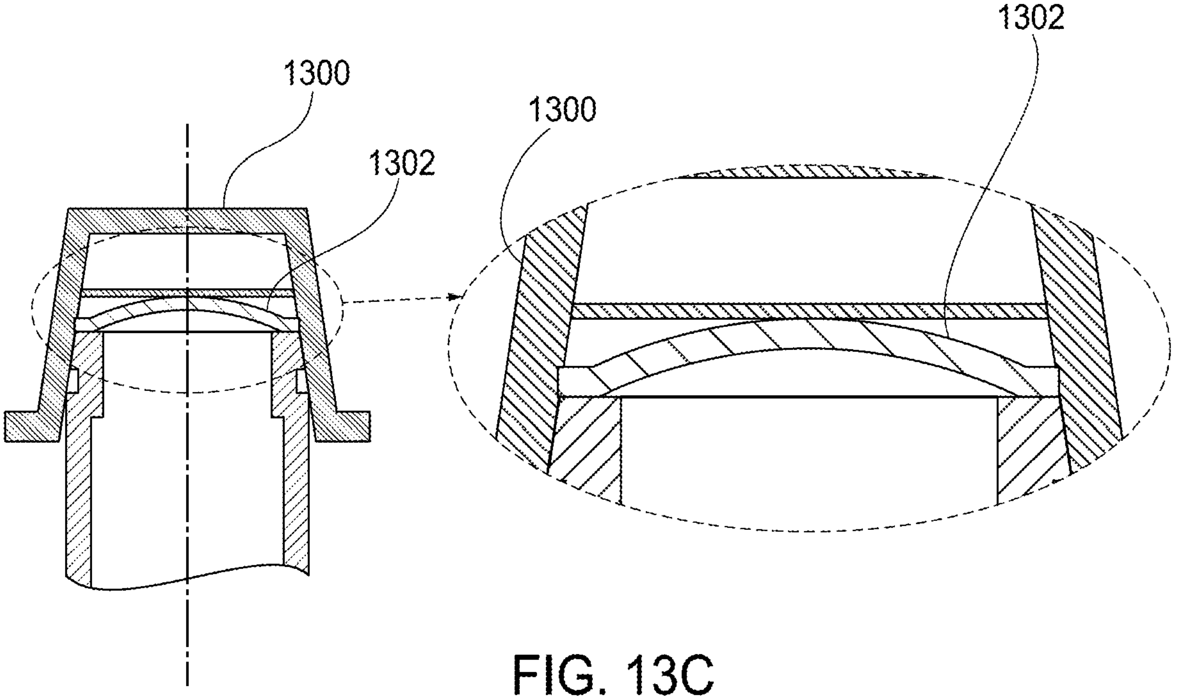

In some non-limiting embodiments or aspects, and referring also to FIGS. 13A-13C, the medical device includes a disinfectant cap 1300. For example, the disinfectant cap 1300 may include a switch 1302 (e.g., a bi-stable metal dome switch, etc.), and the operation of the disinfectant cap 1300 may include a connection of the disinfectant cap 1300 to the needleless connector 214. As an example, connection of the disinfectant cap 1300 to the needleless connector 214 may generate the sound signature when the state of the disinfectant cap 1300 includes the unused state, and, when the state of the disinfectant cap 1300 includes the used state, the connection of the disinfectant cap 1300 to the needleless connector 214 one of: (i) does not generate the sound signature and (ii) generates another sound signature different than the sound signature generated when the state of the disinfectant cap 1300 includes the unused state. In such an example, a bi-stable metal dome switch incorporated in disinfectant cap 1300 may create a sound signature (e.g., a tick or click sound, etc.) when the disinfectant cap 1300 is attached to a connector, and due to the bi-stable nature, the dome switch stays in position and does not provide a sound signature when the disinfectant cap 1300 is re-used, which may enable detection of disinfectant cap re-use (e.g., if a cap attachment is detected by smart device 104 without the tick or click sound, smart device 104 may determine that the cap is being re-used and/or provide an indication of the re-use, etc.).

In some non-limiting embodiments or aspects, sensor 254 includes an identification sensor configured to detect an identification tag on a medical device connected to or being connected to the needleless connector. For example, the identification sensor may include a magnetometer, and the identification tag may include a magnetic material on and/or integrated with needleless connector 214.

In some non-limiting embodiments or aspects, sensor 254 includes a position sensor configured to detect movement of the needleless connector. For example, a movement of the patient, a fall event of the patient, a movement of a bed of the patient may be determined (e.g., by smart device 104, etc.) based on the detected movement of the needleless connector.

In some non-limiting embodiments or aspects, sensor 254 includes an RGB color sensor configured to detect a color of a fluid in the fluid flow path of the needleless connector. For example, at least one of a blood-draw in the needleless connector and a retention of blood in the needleless connector may be determined (e.g., by smart device 104, etc.) based on the color of the fluid detected in the fluid flow path of the needleless connector.

As shown in FIG. 11, at step 1106, process 1100 includes providing an indication of an event. For example, smart device 104 may provide an indication of an event. As an example, smart device 104 may provide an indication of the determined event.

In some non-limiting embodiments or aspects, smart device 104 including needleless connector 214 may include visual indicator 252, and visual indicator 252 may be configured to provide a visual indication associated with the at least one of: the scrubbing event in which the needleless connector is scrubbed with the disinfectant, the flushing event in which the needleless connector is flushed with the solution, the connection event in which the needleless connector is connected to the medical device, the disconnection event in which the needleless connector is disconnected from the medical device, or any combination thereof. For example, as shown in an implementation 600B in FIG. 6B, smart device 104 may provide direct patient-side feedback (e.g., via an LED light to a nurse, etc.) in response to (i) detecting that needleless connector 214 and/or lumen 212 thereof has not been scrubbed for a predetermined period of time and/or before a scheduled use, (ii) detecting that needleless connector 214 and/or lumen 212 thereof has not been scrubbed for a sufficient period of time prior to accessing a catheter line, (iii) detecting that a flush of needleless connector 214 and/or lumen 212 is due, (iv) detecting that a disinfection cap was not attached after a previous access to needleless connector 214 and/or lumen 212, and/or the like. For example, smart device 104 may include needleless connector 214, and needleless connector 214 may be configured to detect at least one of a scrubbing event, a flushing event, a connection or capping event, or any combination thereof. As an example, and needleless connector 214 may be configured to provide information and/or data associated with a detected scrubbing event, a detected flushing event, and/or a detected connection or capping event (e.g., with processor 304, memory 306, storage component 308, input component 310, output component 312, etc.) to store events and report compliance performance for compliance event monitoring.

In some non-limiting embodiments or aspects, smart device 104 may include communication circuitry (e.g., communication interface 314, etc.) that wirelessly transmits the signal (e.g., the force signal, the signal other than the force signal, etc.) and/or an event determined based thereon to a remote computing system. As an example, smart device 104 may process the signal on a microprocessor within a housing of smart device 104 including sensor 254 and the microprocessor, and/or smart device 104 may wirelessly transmit (and/or transmit via wired connection) the signal to a remote computer that performs digital signal processing on the signal, to identify and classify events of interest (e.g., a scrubbing event, a flushing event, a connection event, a disconnection event, a dwell or connection time, etc.).

In some non-limiting embodiments or aspects, a pattern of events including a plurality of the least one of: the scrubbing event in which needleless connector 214 is scrubbed with the disinfectant, the flushing event in which needleless connector 214 is flushed with the solution, connection or capping event in which needleless connector 214 is connected to the medical device, or any combination thereof, may be determined based on the signal (e.g., the force signal, the signal other than a force signal, etc.), and, based on the pattern of events, a medication administration event in which a medication is administered to a patient via needleless connector 214 may be determined.

In some non-limiting embodiments or aspects, smart device 104 may use sensor 254 to detect an identification tag on a medical device connected to or being connected to the needleless connector, movement of the needleless connector, a color of a fluid in the fluid flow path of the needleless connector, or any combination thereof, and provide, with visual indicator 252 visual indication associated with the any information or data sensed and/or measured by sensor 254, such as, a type of the medical device, a medication administration event in which a medication is administered to a patient via the needleless connector, an identification of a medical device, a movement of the patient, a patient fall event, a movement of a bed of the patient, a color of a fluid in the fluid flow path of needleless connector 412, a blood-draw in the needleless connector, a retention of blood in the needleless connector, a scrubbing event in which the needleless connector is scrubbed with a disinfectant, a flushing event in which the needleless connector is flushed with a solution, a connection or capping event in which the needleless connector is connected to a medical device, or any combination thereof.

Although embodiments or aspects have been described in detail or the purpose of illustration and description, it is to be understood that such detail is solely for that purpose and that embodiments or aspects are not limited to the disclosed embodiments or aspects, but, on the contrary, are intended to cover modifications and equivalent arrangements that are within the spirit and scope of the appended claims. For example, it is to be understood that the present disclosure contemplates that, to the extent possible, one or more features of any embodiment or aspect can be combined with one or more features of any other embodiment or aspect. In fact, many of these features can be combined in ways not specifically recited in the claims and/or disclosed in the specification. Although each dependent claim listed below may directly depend on only one claim, the disclosure of possible implementations includes each dependent claim in combination with every other claim in the claim set.

What is claimed is:

1. A system, comprising:

a needleless connector including an inlet, an outlet, and a fluid flow path between the inlet and the outlet;

a catheter including a catheter lumen configured to deliver fluid to a patient, wherein the catheter lumen is in fluid communication with the fluid flow path;

at least one force sensor connected to the needleless connector; and one or more processors programmed and/or configured to:

receive, from the force sensor, a force signal; and determine, based on the force signal, at least one of: a connection event in which the inlet of the needleless connector is connected to a medical device, a disconnection event in which the inlet of the needleless connector is disconnected from the medical device, or any combination thereof.

2. The system of claim 1, further comprising:

communication circuitry configured to transmit the force signal to a remote computing system.

3. The system of claim 1, wherein the at least one force sensor includes at least one of: a piezoelectric element, a force sensitive resistive (FSR) sensor, a strain gauge, or any combination thereof.

4. The system of claim 1, wherein the at least one force sensor is positioned between an outer surface of an inner wall of the needleless connector defining the fluid flow path of the needleless connector and an inner surface of an outer wall of the needleless connector surrounding the inner wall of the needleless connector.

5. The system of claim 4, wherein the at least one force sensor comprises a plurality of force sensors positioned around the fluid flow path of the needleless connector between the inner wall of the needleless connector defining the fluid flow path of the needleless connector and the inner surface of the outer wall of the needleless connector surrounding the inner wall of the needleless connector.

6. The system of claim 1, wherein the inlet of the needleless connector includes a septum including a surface facing in a first direction, wherein the at least one of the force sensor is configured to detect a force in a second direction perpendicular to the surface of the septum facing in the first direction.

7. The system of claim 1, wherein the at least one force sensor includes a pressure sensor, wherein the pressure sensor is one of: in direct contact with a fluid in the fluid flow path of the needleless connector; located within an inner wall of the needleless connector defining the fluid flow path of the needleless connector, and located within a wall of a lumen connected to the needleless connector.

8. The system of claim 1, further comprising:

an optical sensor configured to detect at least one of a color signature and a reflectance of the medical device, and wherein the one or more processors are further programmed and/or configured to:

determine, based on the at least one of the color signature and the reflectance of the medical device, a type of the medical device.

9. The system of claim 1, wherein the one or more processors are further programmed or configured to:

determine, based on the force signal, a pattern of events including a plurality of the least one of: the connection event in which the inlet of the needleless connector is connected to the medical device, the disconnection event in which the inlet of the needleless connector is disconnected from the medical device, or any combination thereof; and determine, based on the pattern of events, a medication administration event in which a medication is administered to a patient via the needleless connector.

10. The system of claim 1, further comprising:

an identification sensor configured to detect an identification tag on a medical device connected to or being connected to the needleless connector.

11. The system of claim 10, wherein the identification sensor includes a magnetometer, and wherein the identification tag includes a magnetic material.

12. The system of claim 1, further comprising:

a positional sensor configured to detect movement of the needleless connector, wherein the one or more processors are further programmed and/or configured to:

determine, based on the detected movement of the needleless connector, at least one of: a movement of the patient and a movement of a bed of the patient.

13. The system of claim 1, further comprising:

a color sensor configured to detect a color of a fluid in the fluid flow path of the needleless connector, wherein the one or more processors are further programmed and/or configured to:

determine, based on the color of the fluid detected in the fluid flow path of the needleless connector, at least one of a blood-draw in the needleless connector and a retention of blood in the needleless connector.

14. The system of claim 1, further comprising:

a visual indicator configured to provide a visual indication associated with the at least one of: the connection event in which the inlet of the needleless connector is connected to the medical device, the disconnection event in which the inlet of the needleless connector is disconnected from the medical device, or any combination thereof.

15. A method, comprising:

coupling a needleless connector to a catheter, the catheter including a catheter lumen configured to deliver fluid to a patient, the needleless connector including a fluid flow path in fluid communication with the catheter lumen;

measuring, with at least one force sensor connected to the needleless connector, a force signal;

receiving, with at least one processor from the at least one force sensor, the force signal; and determining, with at least one processor, based on the force signal, at least one of: a connection event in which the needleless connector is connected to a medical device, a disconnection event in which the needleless connector is disconnected from the medical device, or any combination thereof.

16. The method of claim 15, further comprising:

transmitting, with communication circuitry, the force signal to a remote computing system.

17. The method of claim 15, wherein the at least one force sensor includes at least one of: a piezoelectric element, a force sensitive resistive (FSR) sensor, a strain gauge, or any combination thereof.

18. The method of claim 15, wherein the at least one force sensor is positioned between an outer surface of an inner wall of the needleless connector defining the fluid flow path of the needleless connector and an inner surface of an outer wall of the needleless connector surrounding the inner wall of the needleless connector.

19. The method of claim 18, wherein the at least one force sensor comprises a plurality of force sensors positioned around the fluid flow path of the needleless connector between the inner wall of the needleless connector defining the fluid flow path of the needleless connector and the inner surface of the outer wall of the needleless connector surrounding the inner wall of the needleless connector.

20. The method of claim 15, wherein a first end of the needleless connector includes a septum including a surface facing in a first direction, wherein the force sensor is configured to detect a force in a second direction perpendicular to the surface of the septum facing in the first direction.

21. The method of claim 15, wherein the at least one force sensor includes a pressure sensor, wherein the pressure sensor is one of: in direct contact with a fluid in the fluid flow path of the needleless connector; located within an inner wall of the needleless connector defining the fluid flow path of the needleless connector, and located within a wall of a lumen connected to the needleless connector.

22. The method of claim 15, further comprising:

detecting, with an optical sensor, at least one of a color signature and a reflectance of the medical device; and determining, with at least one processor, based on the at least one of the color signature and the reflectance of the medical device, a type of the medical device.

23. The method of claim 15, further comprising:

determining, with at least one processor, based on the force signal, a pattern of events including a plurality of the least one of: the connection event in which the needleless connector is connected to the medical device, the disconnection event in which the needleless connector is disconnected from the medical device, or any combination thereof; and determining, with at least one processor, based on the pattern of events, a medication administration event in which a medication is administered to a patient via the needleless connector.

24. The method of claim 15, further comprising:

detecting, with an identification sensor, an identification tag on a medical device connected to or being connected to the needleless connector.

25. The method of claim 24, wherein the identification sensor includes a magnetometer, and wherein the identification tag includes a magnetic material.

26. The method of claim 15, further comprising:

detecting, with a positional sensor, movement of the needleless connector; and determining, with at least one processor, based on the detected movement of the needleless connector, at least one of: a movement of the patient and a movement of a bed of the patient.

27. The method of claim 15, further comprising:

detecting, with a color sensor, a color of a fluid in the fluid flow path of the needleless connector; and determining, based on the color of the fluid detected in the fluid flow path of the needleless connector, at least one of a blood-draw in the needleless connector and a retention of blood in the needleless connector.

28. The method of claim 15, further comprising:

providing, with a visual indicator, a visual indication associated with the at least one of: the connection event in which the needleless connector is connected to the medical device, the disconnection event in which the needleless connector is disconnected from the medical device, or any combination thereof.

* * * * *